(12) United States Patent
Justis et al.

(10) Patent No.: US 7,771,476 B2
(45) Date of Patent: Aug. 10, 2010

(54) CURABLE ORTHOPEDIC IMPLANT DEVICES CONFIGURED TO HARDEN AFTER PLACEMENT IN VIVO BY APPLICATION OF A CURE-INITIATING ENERGY BEFORE INSERTION

(75) Inventors: Jeff R. Justis, Collierville, TN (US); Hai H. Trieu, Cordova, TN (US); Dimitri Protopsaltis, Memphis, TN (US); Michael C. Sherman, Memphis, TN (US)

(73) Assignee: Warsaw Orthopedic Inc.

( * ) Notice: Subject to any disclaimer, the term of this patent is extended or adjusted under 35 U.S.C. 154(b) by 806 days.

(21) Appl. No.: 11/643,489

(22) Filed: Dec. 21, 2006

(65) Prior Publication Data

US 2008/0154368 A1 Jun. 26, 2008

(51) Int. Cl.
*A61F 2/44* (2006.01)

(52) U.S. Cl. ............... 623/17.11; 623/13.15; 623/17.16; 623/11.11

(58) Field of Classification Search .............. 606/60, 606/61, 192, 62; 623/11.11, 17.11–17.16, 623/13.15
See application file for complete search history.

(56) References Cited

U.S. PATENT DOCUMENTS

| | | | |
|---|---|---|---|
| 2,267,925 | A | 12/1941 | Johnston |
| 3,155,091 | A | 11/1964 | Nissenbaum et al. |
| 3,834,394 | A | 9/1974 | Hunter et al. |
| 3,875,595 | A | 4/1975 | Froning |
| 3,877,424 | A | 4/1975 | Murray |
| 4,041,939 | A | 8/1977 | Hall |
| 4,064,566 | A | 12/1977 | Fletcher et al. |
| 4,085,757 | A | 4/1978 | Pevsner |
| 4,289,123 | A | 9/1981 | Dunn |
| 4,327,734 | A | 5/1982 | White, Jr. |
| 4,341,218 | A | 7/1982 | Ü |
| 4,346,712 | A | 8/1982 | Handa et al. |
| 4,364,392 | A | 12/1982 | Strother et al. |
| 4,383,879 | A | 5/1983 | Le Du et al. |

(Continued)

FOREIGN PATENT DOCUMENTS

DE 3924990 2/1991

(Continued)

OTHER PUBLICATIONS

Katsuya Goto et al., "Permanent Inflation of Detachable Balloons with a Low-Viscosity, Hydrophilic Polymerizing System", Radiology, Dec. 1988; 169:787-790.

(Continued)

*Primary Examiner*—Eduardo C Robert
*Assistant Examiner*—Christina Negrelli

(57) ABSTRACT

An orthopedic implant device is non-rigid, i.e., flexible and/or malleable, in a first form for insertion into a desired in vivo site, and then transformable into a rigid, or hardened, form for providing a load-bearing function or providing other structural and/or mechanical function after implant. The device includes a biocompatible sheath and a curable material sealed within the sheath. The curable material is provided in a first form that provides flexibility to the device and is structured to rigidize in a second form after insertion to an in vivo location as a result of application of a cure-initiating energy to the material prior to insertion. Related methods and kits are also provided.

34 Claims, 16 Drawing Sheets

U.S. PATENT DOCUMENTS

| | | |
|---|---|---|
| 4,441,495 A | 4/1984 | Hicswa |
| 4,471,779 A | 9/1984 | Antoshkiw et al. |
| 4,517,979 A | 5/1985 | Pecenka |
| 4,545,367 A | 10/1985 | Tucci |
| 4,547,168 A | 10/1985 | Blacksberg et al. |
| 4,612,384 A | 9/1986 | Omura et al. |
| 4,638,803 A | 1/1987 | Rand |
| RE32,348 E | 2/1987 | Pevsner |
| 4,643,733 A | 2/1987 | Becker |
| 4,648,388 A | 3/1987 | Stefee |
| 4,686,973 A | 8/1987 | Frisch |
| 4,693,721 A | 9/1987 | Ducheyne |
| 4,714,721 A | 12/1987 | Franek et al. |
| 4,743,260 A | 5/1988 | Burton |
| 4,772,287 A | 9/1988 | Ray et al. |
| 4,772,289 A | 9/1988 | Anzinger et al. |
| 4,819,637 A | 4/1989 | Dormandy, Jr. et al. |
| 4,832,680 A | 5/1989 | Haber et al. |
| 4,887,595 A | 12/1989 | Heinig et al. |
| 4,888,022 A | 12/1989 | Huebsch |
| 4,892,550 A | 1/1990 | Huebsch |
| 4,893,618 A | 1/1990 | Herzberg |
| 4,904,260 A | 2/1990 | Ray et al. |
| 4,963,151 A | 10/1990 | Ducheyne et al. |
| 4,998,936 A | 3/1991 | Mehdian |
| 5,000,165 A | 3/1991 | Watanabe |
| 5,002,556 A | 3/1991 | Ishida et al. |
| 5,002,576 A | 3/1991 | Fuhrmann et al. |
| 5,030,220 A | 7/1991 | Howland |
| 5,037,445 A | 8/1991 | Sander et al. |
| 5,084,049 A | 1/1992 | Asher et al. |
| 5,084,051 A | 1/1992 | Törmälä et al. |
| 5,106,360 A | 4/1992 | Ishiwara et al. |
| 5,108,404 A | 4/1992 | Scholten et al. |
| 5,139,499 A | 8/1992 | Small et al. |
| 5,141,521 A | 8/1992 | Wenner |
| 5,146,933 A | 9/1992 | Boyd |
| 5,165,919 A | 11/1992 | Sasaki et al. |
| 5,171,279 A | 12/1992 | Mathews |
| 5,171,280 A | 12/1992 | Baumgartner |
| 5,176,680 A | 1/1993 | Vignaud et al. |
| 5,181,921 A | 1/1993 | Makita et al. |
| 5,190,540 A | 3/1993 | Lee |
| 5,195,970 A | 3/1993 | Gahara |
| 5,222,970 A | 6/1993 | Reeves |
| 5,242,443 A | 9/1993 | Kambin |
| 5,242,444 A | 9/1993 | MacMillan |
| 5,304,123 A | 4/1994 | Atala et al. |
| 5,306,275 A | 4/1994 | Bryan |
| 5,320,529 A | 6/1994 | Pompa |
| 5,324,261 A | 6/1994 | Amundson et al. |
| 5,342,361 A | 8/1994 | Yuan et al. |
| 5,344,398 A | 9/1994 | Hara |
| 5,357,983 A | 10/1994 | Mathews |
| 5,366,490 A | 11/1994 | Edwards et al. |
| 5,397,363 A | 3/1995 | Gelbard |
| 5,464,407 A | 11/1995 | McGuire |
| 5,468,245 A | 11/1995 | Vargas, III |
| 5,470,336 A | 11/1995 | Ling et al. |
| 5,474,551 A | 12/1995 | Finn et al. |
| 5,484,418 A | 1/1996 | Quiachon et al. |
| 5,486,174 A | 1/1996 | Fournet-Fayard et al. |
| 5,496,322 A | 3/1996 | Mathews |
| 5,520,689 A | 5/1996 | Schläpfer et al. |
| 5,529,653 A | 6/1996 | Glastra |
| 5,549,679 A | 8/1996 | Kuslich |
| 5,554,191 A | 9/1996 | Lahille et al. |
| 5,556,429 A | 9/1996 | Felt |
| 5,562,661 A | 10/1996 | Yoshimi et al. |
| 5,562,736 A | 10/1996 | Ray et al. |
| 5,569,248 A | 10/1996 | Mathews |
| 5,571,189 A | 11/1996 | Kuslich |
| 5,584,887 A | 12/1996 | Kambin |
| 5,591,165 A | 1/1997 | Jackson |
| 5,591,167 A | 1/1997 | Laurain et al. |
| 5,591,199 A | 1/1997 | Porter et al. |
| 5,593,408 A | 1/1997 | Gayet et al. |
| 5,649,925 A | 7/1997 | Alacreu |
| 5,658,289 A | 8/1997 | Boucher et al. |
| 5,681,872 A | 10/1997 | Erbe |
| 5,702,373 A | 12/1997 | Samson |
| 5,720,751 A | 2/1998 | Jackson |
| 5,728,097 A | 3/1998 | Mathews |
| 5,733,260 A | 3/1998 | DeMaio et al. |
| 5,752,955 A | 5/1998 | Errico |
| 5,772,661 A | 6/1998 | Michelson |
| 5,772,681 A | 6/1998 | Leoni |
| 5,776,099 A | 7/1998 | Tremulis |
| 5,779,672 A | 7/1998 | Dormandy, Jr. |
| 5,792,044 A | 8/1998 | Foley et al. |
| 5,792,106 A | 8/1998 | Mische |
| 5,795,353 A | 8/1998 | Felt |
| 5,800,435 A | 9/1998 | Errico et al. |
| 5,827,289 A | 10/1998 | Reiley et al. |
| 5,837,752 A | 11/1998 | Shastri et al. |
| 5,840,059 A | 11/1998 | March et al. |
| 5,865,848 A | 2/1999 | Baker |
| 5,879,713 A | 3/1999 | Roth et al. |
| 5,888,220 A | 3/1999 | Felt et al. |
| 5,899,939 A | 5/1999 | Boyce et al. |
| 5,910,142 A | 6/1999 | Tatar |
| 5,914,356 A | 6/1999 | Erbe |
| 5,938,663 A | 8/1999 | Petreto |
| 5,972,015 A | 10/1999 | Scribner et al. |
| 5,980,522 A | 11/1999 | Koros et al. |
| 5,980,523 A | 11/1999 | Jackson |
| 6,025,406 A | 2/2000 | Oxman et al. |
| 6,033,406 A | 3/2000 | Mathews |
| 6,042,380 A | 3/2000 | De Rowe |
| 6,043,295 A | 3/2000 | Oxman et al. |
| 6,048,343 A | 4/2000 | Mathis et al. |
| 6,066,154 A | 5/2000 | Reiley et al. |
| 6,080,801 A | 6/2000 | Draenert et al. |
| 6,099,528 A | 8/2000 | Saurat |
| 6,102,912 A | 8/2000 | Cazin et al. |
| 6,106,530 A | 8/2000 | Harada |
| 6,123,707 A | 9/2000 | Wagner |
| 6,126,689 A | 10/2000 | Brett |
| 6,127,597 A | 10/2000 | Beyar et al. |
| 6,140,452 A | 10/2000 | Felt et al. |
| 6,149,655 A | 11/2000 | Constantz et al. |
| 6,159,012 A | 12/2000 | Oxman et al. |
| 6,174,334 B1 | 1/2001 | Suddaby |
| 6,175,758 B1 | 1/2001 | Kambin |
| 6,176,882 B1 | 1/2001 | Biedermann et al. |
| 6,183,515 B1 | 2/2001 | Barlow et al. |
| 6,187,048 B1 * | 2/2001 | Milner et al. ............ 623/17.12 |
| 6,206,922 B1 | 3/2001 | Zdeblick et al. |
| 6,226,548 B1 | 5/2001 | Foley et al. |
| 6,235,028 B1 | 5/2001 | Brumfield et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,270,515 B1 | 8/2001 | Linden et al. |
| 6,280,456 B1 | 8/2001 | Scribner et al. |
| 6,293,960 B1 | 9/2001 | Ken |
| 6,296,643 B1 | 10/2001 | Hopf et al. |
| 6,306,177 B1 | 10/2001 | Felt et al. |
| 6,309,421 B1 | 10/2001 | Pisharodi |
| 6,332,894 B1 | 12/2001 | Stalcup et al. |
| 6,379,329 B1 | 4/2002 | Naglreiter et al. |
| 6,395,034 B1 | 5/2002 | Suddaby |
| 6,402,784 B1 | 6/2002 | Wardlaw |
| 6,425,923 B1 | 7/2002 | Stalcup et al. |

| | | |
|---|---|---|
| 6,443,988 B2 | 9/2002 | Felt et al. |
| 6,447,514 B1 | 9/2002 | Stalcup et al. |
| 6,530,926 B1 | 3/2003 | Davison |
| 6,530,929 B1 | 3/2003 | Justis et al. |
| 6,547,804 B2 | 4/2003 | Porter et al. |
| 6,558,386 B1 | 5/2003 | Cragg |
| 6,558,390 B2 | 5/2003 | Cragg |
| 6,666,870 B2 | 12/2003 | Dixon et al. |
| 6,726,691 B2 | 4/2004 | Osorio et al. |
| 6,749,614 B2 | 6/2004 | Teitelbaum et al. |
| 6,805,695 B2 | 10/2004 | Keith et al. |
| 6,821,277 B2 | 11/2004 | Teitelbaum |
| 6,893,466 B2 | 5/2005 | Trieu |
| 6,899,713 B2 | 5/2005 | Shaolian et al. |
| 6,932,843 B2 | 8/2005 | Smith et al. |
| 6,958,077 B2 | 10/2005 | Suddaby |
| 6,964,667 B2 | 11/2005 | Shaolian et al. |
| 6,969,405 B2 | 11/2005 | Suddaby |
| 6,987,136 B2 | 1/2006 | Erbe et al. |
| 7,001,431 B2 | 2/2006 | Bao et al. |
| 7,004,971 B2 | 2/2006 | Serhan et al. |
| 7,077,865 B2 | 7/2006 | Bao et al. |
| 2001/0004710 A1 | 6/2001 | Felt et al. |
| 2002/0022764 A1 | 2/2002 | Smith et al. |
| 2002/0045904 A1 | 4/2002 | Fuss et al. |
| 2002/0068975 A1 | 6/2002 | Teitelbaum et al. |
| 2002/0082598 A1 | 6/2002 | Teitelbaum |
| 2002/0082600 A1 | 6/2002 | Shaolian et al. |
| 2002/0082601 A1 | 6/2002 | Toyama et al. |
| 2002/0095158 A1 | 7/2002 | Dixon et al. |
| 2002/0123750 A1 | 9/2002 | Eisermann et al. |
| 2002/0161368 A1 | 10/2002 | Foley et al. |
| 2002/0165572 A1 | 11/2002 | Saadat |
| 2002/0198526 A1 | 12/2002 | Shaolian et al. |
| 2003/0028251 A1 | 2/2003 | Mathews |
| 2003/0040800 A1 | 2/2003 | Li et al. |
| 2003/0060826 A1 | 3/2003 | Foley et al. |
| 2003/0087984 A1 | 5/2003 | Erbe et al. |
| 2003/0125739 A1 | 7/2003 | Bagga et al. |
| 2003/0144624 A1 | 7/2003 | Barbut |
| 2003/0167967 A1 | 9/2003 | Narhi et al. |
| 2003/0171451 A1 | 9/2003 | White et al. |
| 2003/0195547 A1 | 10/2003 | Scribner et al. |
| 2003/0220666 A1 | 11/2003 | Mirigian et al. |
| 2004/0006341 A1 | 1/2004 | Shaolian et al. |
| 2004/0087950 A1 | 5/2004 | Teitelbaum |
| 2004/0092948 A1 | 5/2004 | Stevens et al. |
| 2004/0230309 A1 | 11/2004 | DiMauro et al. |
| 2005/0010220 A1 | 1/2005 | Casutt et al. |
| 2005/0027257 A1 | 2/2005 | Davey |
| 2005/0251140 A1 * | 11/2005 | Shaolian et al. ............... 606/61 |
| 2005/0273178 A1 | 12/2005 | Boyan et al. |
| 2006/0106459 A1 | 5/2006 | Truckai et al. |

FOREIGN PATENT DOCUMENTS

| | | |
|---|---|---|
| DE | 197 26 754 A1 | 2/1999 |
| EP | 1 132 053 | 9/2001 |
| EP | 1 421 921 | 5/2004 |
| GB | 2086231 | 5/1982 |
| JP | 2005028046 | 2/2005 |
| NL | 9001858 | 3/1992 |
| SU | 839513 | 5/1981 |
| SU | 1745231 A1 | 7/1992 |
| WO | WO 89/09031 | 10/1989 |
| WO | WO 97/30666 | 8/1997 |
| WO | WO 97/38639 | 10/1997 |
| WO | WO 99/09902 | 3/1999 |
| WO | WO 99/15097 | 4/1999 |
| WO | WO 99/26549 | 6/1999 |
| WO | WO 00/44288 | 8/2000 |
| WO | WO 02/00126 | 1/2002 |
| WO | WO 2004/017857 | 3/2004 |
| WO | WO 2004/058045 | 7/2004 |
| WO | WO 2006/063083 | 6/2006 |
| WO | WO 2006/074410 | 7/2006 |

OTHER PUBLICATIONS

European Search Report for Application No. PCT/US0227516 mailed on Aug. 25, 2009.

* cited by examiner

CURABLE ORTHOPEDIC IMPLANT DEVICES CONFIGURED TO HARDEN AFTER PLACEMENT IN VIVO BY APPLICATION OF A CURE-INITIATING ENERGY BEFORE INSERTION

BACKGROUND

The present application relates to the field of orthopedic implants and manners of positioning same at desired in vivo locations. More particularly, the application relates to devices, systems and implants for treatment of spinal deformities and conditions, or other skeletal deformities and conditions. The devices can be used to treat either chronic or acute conditions.

The use of prosthetic implants to address orthopedic injuries and ailments has become commonplace. While bone wounds can regenerate, fractures and other orthopedic injuries take a substantial time to heal, during which the bone is unable to support physiologic loads. It is well understood that stabilization of adjacent bony portions can be completed with an implant positioned between the bony portions and/or an implant positioned along the bony portions. A wide variety of orthopedic implant devices are known that are designed to provide structural support to a patient's spine or other bone or joint. The implants can be rigid to prevent motion between the bony portions, or can be flexible to allow at least limited motion between the bony portions while providing a stabilizing effect. As used herein, bony portions can be portions of bone that are separated by one or more joints, fractures, breaks, or other space. Implants can be positioned, for example, for use in rigid posterior spinal fixation systems, such as rods, plates, tethers and staples; for use in interbody spinal fusion or corpectomy; for use in dynamic spinal stabilization; or for rigid or dynamic stabilization of other bones or skeletal joints. In addition, pins, screws and meshes are frequently used in devices that replace the mechanical functions of injured bone during the time of bone healing and regeneration.

In this arena, it is often desired to decrease the invasiveness of implant placement procedures, improve implant integrity, and provide more positive patient outcomes. Particularly, it is often desired to provide an implant with reduced dimensions and/or flexible characteristics to facilitate implantation while also providing sufficient rigidity to provide support for corrective treatment. Unfortunately, current devices can be limiting in certain applications. Thus, there is a need for additional contributions in this area of technology.

SUMMARY

The present application provides a variety of orthopedic implant devices that are malleable and/or flexible during the implant procedure and then hardened at the site of the implant. Thus, a device has a first state that provides more flexibility than a second state. Other aspects include unique methods, systems, devices, instrumentation, and apparatus involving the subject orthopedic implant devices.

In one aspect of the application, an orthopedic implant device includes a biocompatible sheath and a curable material having a non-rigid form contained and sealed in the sheath. The device is deformable before and during implantation within a patient, the curable material is transformable to a rigid form after application of a quantity of an initiating energy to the material effective to cure the material, and the curable material exhibits a working time of at least 1 minute after application of the energy and prior to fully transforming to the rigid form.

In another aspect of the application, an orthopedic implant device includes a biocompatible sheath; a curable material contained within the sheath, the curable material operable, upon application of a cure-initiating energy, to harden, thereby forming a load-bearing component of an orthopedic implant, and wherein the curable material exhibits a working time of at least 1 minute after application of the energy and prior to fully transforming to the rigid form; and an energy delivery element contained within the sheath, the energy delivery element operable to deliver initiating energy to the curable material.

In yet another aspect, the application provides an orthopedic implant device that includes a biocompatible sheath and a curable material contained within the biocompatible sheath, the curable material operable, upon application of a quantity of a cure-initiating energy, to harden, thereby forming a load-bearing component of an orthopedic implant. The curable material exhibits a working time of at least 1 minute after application of the energy and prior to fully transforming to the rigid form, the initiating energy is electromagnetic radiation of a predetermined wavelength, and the sheath is transparent to the radiation.

The application also provides an orthopedic implant device that includes a biocompatible sheath, a pressurizeable balloon contained within the sheath; and a curable material contained within the sheath external to the balloon, the curable material operable, upon application of a quantity of a cure-initiating energy, to harden, thereby forming a load-bearing component of an orthopedic implant. The curable material exhibits a working time of at least 1 minute after application of the energy and prior to fully transforming to the rigid form, and the balloon is operable to receive a pressurizing fluid to pressurize the balloon and exert an outward pressure on the curable material and the sheath.

In still another aspect, the application provides an orthopedic implant device that includes a biocompatible sheath; a curable material contained within the biocompatible sheath, the curable material operable, upon application of a quantity of a cure-initiating energy to the curable material, to harden, thereby forming a load-bearing component of an orthopedic implant, wherein the curable material exhibits a working time of at least 1 minute after application of the energy and prior to fully transforming to the rigid form; and an internal reinforcement member contained within a biocompatible sheath.

In yet another aspect of the application, there is provided an orthopedic implant device that includes a flexible means for containing a curable material and a curable means contained in said containing means for imparting malleability to the device during a pre-cured period of time and rigidity during a post-cured period. The curable means is cured to impart rigidity by application of an initiating energy, the curable means exhibits a working time of at least 1 minute after application of the energy and prior to fully transforming to a rigid form, and the device is deformable before and during implantation within a patient.

The application also provides an orthopedic implant kit that includes: (1) a device including a biocompatible sheath and a curable material having a non-rigid form contained and sealed in the sheath, wherein the material is transformable to a rigid form after application of a quantity of an initiating energy to the material effective to fully cure the material, and wherein the curable material exhibits a working time of at least 1 minute after application of the energy and prior to fully transforming to the rigid form; and (2) instructions, recorded in a tangible medium, for positioning the device in an in vivo location where the provision of load-bearing functionality is desired and applying a cure-initiating energy to the curable material after the device is positioned in the in vivo location.

In another aspect, the application provides a method for making an orthopedic implant device, comprising: (1) providing a material in a non-rigid form, wherein the material is effective to transform to a rigid form after application of an initiating energy to the material, and wherein the curable material exhibits a working time of at least 1 minute after application of the energy and prior to fully transforming to the rigid form; and (2) sealing the material in a biocompatible sheath to provide a self-contained, malleable device.

Further embodiments, forms, features and aspects of the present application shall become apparent from the detailed description and figures provided herewith.

DESCRIPTION OF THE ILLUSTRATED EMBODIMENTS

Figure 1:
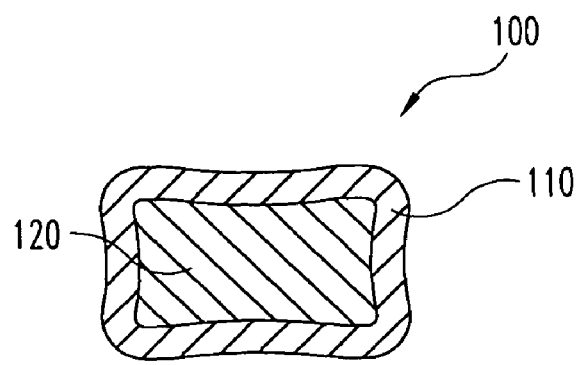
FIG. 1 is a cross sectional view of one embodiment of an implant device.

For the purposes of promoting an understanding of the principles of the inventions described herein, reference will now be made to the embodiments illustrated in the drawings and specific language will be used to describe the same. It will nevertheless be understood that no limitation of the scope of any invention is thereby intended. Any alterations and further modifications in the illustrated embodiments, and any further applications of the principles described and illustrated herein are contemplated as would normally occur to one skilled in the art.

The present application provides implantable orthopedic prosthetic devices that are curable to a hardened form by application of an initiating energy prior to implantation, but that remain malleable for a period of time after application of the initiating energy (referred to herein as the "working time") to provide sufficient time for insertion into a desired in vivo site and placement and formation into a desired location and shape prior to becoming fully hardened. The device contains precursors that are polymerized and/or cross-linked by a reaction that is moderated to allow the device to remain malleable for the working time, before becoming hardened, at which time the device provides a load-bearing function or provides other structural and/or mechanical function. Terms such as "hardenable" or "curable" are used interchangeably herein, and are intended to refer to any material that can be stably stored for an extended period of time in a first, malleable or flexible form without loss of flexibility, and transitionable into a second, hardened form after application of an initiating energy thereto. These terms are not intended to be limited to any specific mechanism of hardening. As will be understood by those of skill in the art, a variety of hardening mechanisms can be utilized, depending upon material selection, including for example, curing that is initiated by ultraviolet radiation, visible light, infrared radiation, radio frequency radiation, x-ray radiation, gamma radiation or other wavelength of electromagnetic energy, catalyst-initiated polymerization, thermally-initiated polymerization, electrically-initiated polymerization, mechanically-initiated polymerization, curing initiated by electron beam radiation and the like.

Orthopedic implants that include at least one malleable device containing a hardenable material, and that are configured to be hardened after placement in a desired in vivo position by application of a cure-initiating energy prior to implantation, find advantageous use in a variety of different circumstances. For example and without limitation, such implants can be used to advantage in circumstances in which it is desirable for medical personnel to shape or re-shape a component during the course of an implantation procedure. The versatility also allows for less invasive technique for orthopedic implantation procedures, allows for greater design flexibility with regard to the implant device, and enables the avoidance of complications that can arise during a wet out or a two-part mixing process during surgery. The embodiments are described primarily by reference to spinal devices; however, it is intended that the application be understood to encompass orthopedic devices used in non-spinal locations as well. Orthopedic implants in accordance with the application find advantageous use, for example, for stabilization of joints, such as hip or knee joints.

Devices contemplated by the application can be malleable, or flexible, prior to the time the curable material therein is exposed to an energy source that initiates curing of the material and for a working time thereafter during which the device is inserted to an in vivo location, and then assume a more rigid state after the device is in position. With reference to FIG. 1, device 100 includes biocompatible sheath 110 and curable material 120 contained and sealed in sheath 110. Curable material 120 has a non-rigid form, and is transformable to a rigid form after application of a quantity of an initiating energy to material 120 that is effective to cure material 120. When device 100 hardens, it becomes a load-bearing component of an orthopedic implant having a desired shape and at a desired position. The component can be, for example, a spinal rod, a plate, a spacer, a bone screw, an anchor, an artificial disk and a nucleus implant. Curable material 120 is sealed within sheath 110 so that injection or other handling or preparation of curable material during a surgical procedure can be avoided, if desired.

The primary functions of sheath 110 are to contain the curable material 120 and to influence or control the shape of device 100, prior to completion of curing. Sheath 110 may comprise all or a portion of the respective implant device surrounding the curable material, and sheath 110, either alone or in conjunction with other materials comprising the body of a device, prevents contact of the curable material with host tissues at least when the curable material is in a malleable form. Sheath 110 is not normally required to restrain pressure over an extended period of time. Thus, significant design flexibility may be permitted. The material from which the sheath is made (also referred to herein as the "sheath material") may be biostable or bioresorbable. For example, sheath 110 may be porous, which can be advantageous for drug delivery or to permit osteoincorporation and/or soft tissue ingrowth. Alternatively, sheath 110 can be designed to have an active agent adsorbed thereon. In yet another alternative form, sheath 110 can be composed of a biodegradable material, optionally having one or more active agents impregnated therein, that is absorbed by natural processes over time after implant. Sheath 110 can be constructed in any of a variety of ways, and may be made out of a wide variety of woven or nonwoven fibers, fabrics, metal mesh such as woven or braided wires, and carbon. Examples of suitable biocompatible sheath material include, for example, polyethylene (PE), polyethylene terephthalate (PET), polyamide, polyurethane, polylactic acid (PLA), PLDLA, ePTFE and Dacron™, to name a few. Other materials from which the sheath can be made include polyester, silicone, polyetheretherketone, polyacrylate, polylactide and polyglycolide. The material can be formed into a variety of forms, including, for example, sheets, tubing, balloons, pouches and fabric, to name a few.

In one embodiment, sheath 110 is energy permeable, and structured such that energy from an energy source external to the device can pass therethrough to contact curable material 120 and initiate curing thereof. In an exemplary embodiment, when curable material 120 is of a type that cures upon exposure to thermal energy, sheath 110 may comprise a biocompatible material that conducts heat and is capable of sealingly enclosing curable material 120. Curing is preferably achieved at a temperature of from about 20° C. to about 70° C. In another embodiment, the curable material comprises a photocurable material that cures when exposed to light or other electromagnetic radiation that passes through the sheath. For such embodiments to cure thoroughly, it is important that the sheath and the curable material itself have suitable properties, such as, for example, transparency and/or translucency and thickness, such that the cure initiating energy can penetrate sufficiently into the curable material to achieve sufficient curing. Of course, a person skilled in the art will recognize that a degree of curing less than complete curing can be sufficient as long as the degree of curing yields a device having sufficient load-bearing strength or sufficient strength for other mechanical function for which the device is used. It is, of course, also appreciated that a given sheath can be provided that is transparent or translucent at certain selected wavelengths of light or other electromagnetic radiation but not others. It is within the purview of a person skilled in the art to select a sheath material and a curable material that are operable together.

To position a load-bearing component as provided herein a malleable device including a biocompatible sheath and a curable material sealed within the sheath is exposed to a dose of initiating energy and then inserted to an in vivo location where the provision of load-bearing functionality is desired. The device has a non-rigid form when exposed and inserted, and is transformable to a rigid form after it is positioned in vivo. Examples of cure-initiating energy that can be used include, for example, electromagnetic radiation, thermal energy, electrical energy, chemical energy and mechanical energy. Device 100 depicted in FIG. 1 is deformable before and during implantation within a patient. Device 100 can be configured in a wide variety of shapes and sizes for a wide variety of end uses after curing of the curable material, such as, for example, as components of extradiscal spinal implant systems, intradiscal spinal implant systems and implant systems for other regions of the body. Further detail regarding certain exemplary embodiments are provided with reference to the Figures, each of which depicts an inventive device that includes a sheath surrounding or adjacent to one or more internal chambers, wherein the internal chamber(s) includes a curable material housed therein. The implant devices illustrated in FIGS. 2-13 and 21-25 are examples of the many types, shapes, forms and configurations of extradiscal implant devices contemplated by the present application, and each of the devices in FIGS. 14-19 are examples of intradiscal implant devices contemplated by the present application. It should be appreciated that the features provided herein can also be applied to other forms, shapes, configurations of other extradiscal implant devices.

Figure 2:
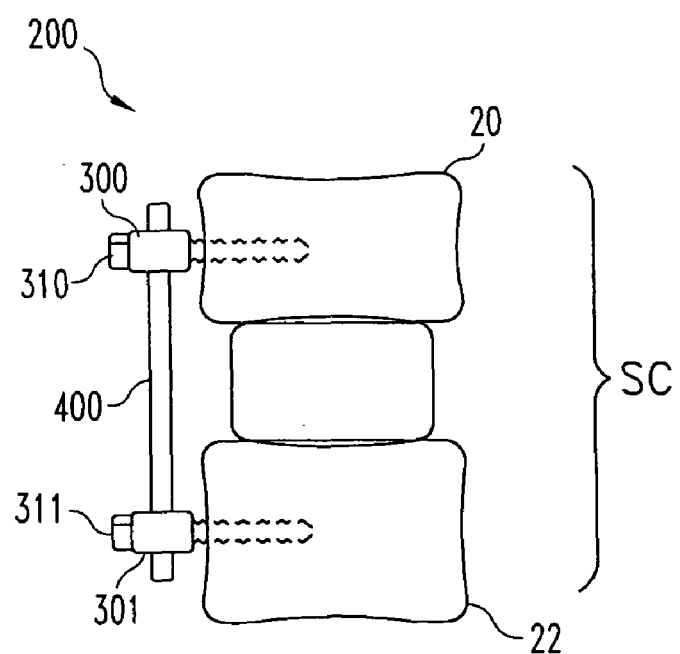
FIG. 2 is a side plan view of an extradiscal spinal implant system relative to the spinal column of a patient.
Figure 10:
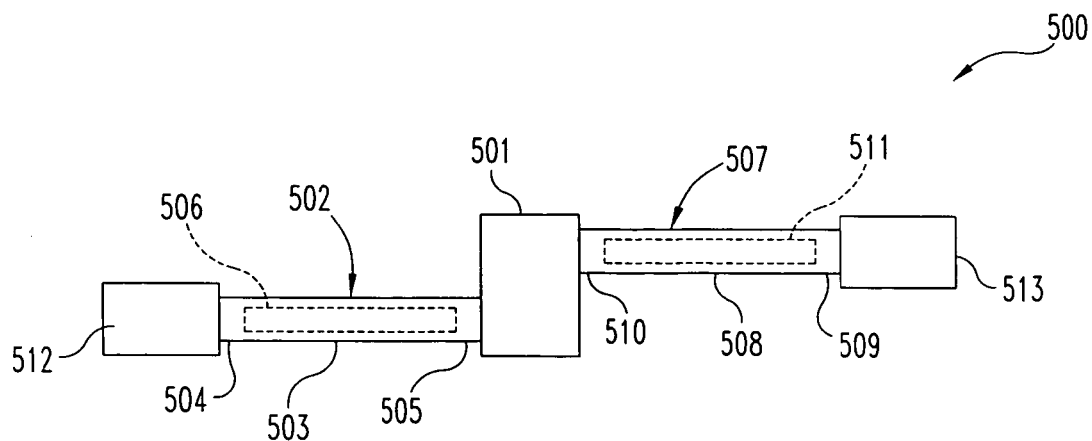
FIG. 10 is a side plan view of a crosslink device which may be used with the spinal implant system of FIG. 2 with some features shown in phantom.

With reference to FIG. 2, there is shown a device that includes an extradiscal spinal implant system 200 in side plan view relative to the spinal column SC of a patient. Spinal implant system 200 includes a pair of anchor devices 300, 301 and an elongate fixation element device in the form of spinal rod 400. Furthermore, as will be appreciated by one having skill in the art, system 200 may include additional components, like for example, a crosslink device 500 as shown in FIG. 10. System 200 may be used for treatment of several spinal deformities, including, but not limited to, treatment of degenerative spondylolisthesis, fracture, dislocation, scoliosis, kyphosis, spinal tumor, and/or a failed previous fusion.

Figure 3:
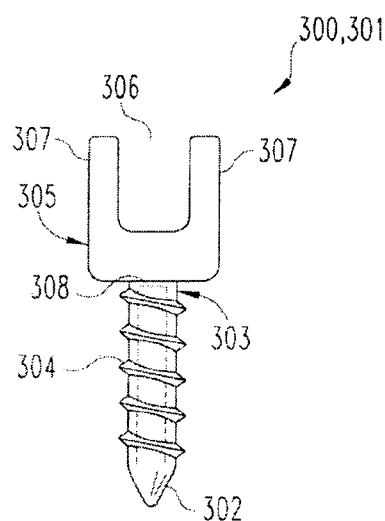
FIG. 3 is a side view of a bone anchor device of the spinal implant system of FIG. 2 with some features shown in phantom.

Anchor devices 300 and 301 are shown in side plan view in FIG. 3 with certain features illustrated in phantom. Anchor devices 300 and 301, respectively, can each have an elongated shaft or stem 303 with bone engaging structures 304. Structures 304 may be in form of threads, spikes, barbs or other structure. A stem without bone engaging structures is also contemplated. Stem 303 is structured to be positioned in and engage a passageway prepared in one or more bones or bony structures in a standard manner, and can be provided with cutting flutes or other structure for self-tapping and/or self-drilling capabilities. Stem 303 can also be cannulated to receive a guidewire to facilitate placement and may further include fenestrations or other openings for placement of bone growth material.

Anchor devices 300, 301 can include a head or a receiver portion 305 defining a receiving channel 306 between upright arms 307. Head or receiver portion 305 can be fixed relative to stem 303 to provide a uni-axial arrangement. Receiving channel 306 is sized and shaped to receive spinal rod 400 and may include structures to engage engaging members 310, 311 for securing spinal rod to head 305, such as internal threading along receiving channel 306 or external threading on head 305, both of which are not shown. In another embodiment, head 305 may include any means for securing spinal rod 400 thereto as would be known to one having skill in the art. As illustrated, receiving channel 306 can be concavely curved and form a passage having a shape of a portion of a circle to receive the rod in form fitting engagement therein. Other embodiments contemplate that the rod is positioned against a proximal head of the stem, or against a cap or crown adjacent a head of the stem, in receiving channel 306. It is further contemplated that receiving channel 306 can be shaped in a variety of configurations to correspond to spinal rod 400 having a non-circular cross section, such as but not limited to, an oval, rectangular, hexagonal, or octagonal cross section.

Figure 4:
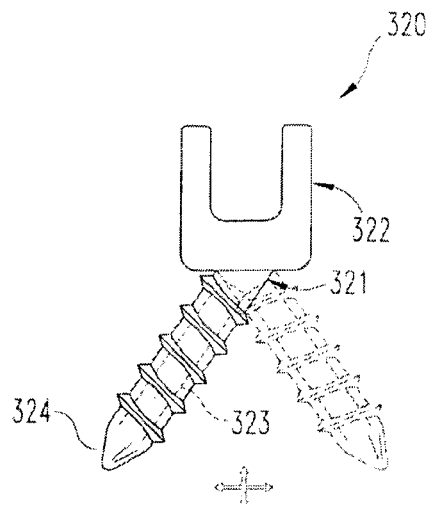
FIG. 4 is a side plan view of an adjustable configuration bone anchor device according to an alternative embodiment of the bone anchor device of FIG. 2, with some features shown in phantom.

Referring now to FIG. 4, another embodiment anchor device 320 is shown. Anchor device 320 can be in the form of a stem portion 321 pivotally captured in head portion 322. Pivotal anchor device 320 may be multi-axial, poly-axial, uni-axial, or uni-planar with respect to the manner in which stem portion 321 and head 322 are movable relative to one another. In one movable form, stem portion 321 and head 322 are engaged together with a "ball and joint" or swivel type of coupling that permits relatively universal movement therebetween during at least some stages of assembly.

In yet another form, implant system 200 may include bone anchors in the form of one or more hooks to engage an adjacent bony structure such as a pedicle, lamina, spinous process, transverse process, or other bony structure suitably engaged with a spinal hook. For instance, a multi-axial laminar hook form of a bone anchor can be used in place of one or more of the anchor devices 300, 301. In still other embodiments, the bone anchor can include a bone attachment structure in the form of a staple, bone plate, interbody fusion device, interbody spacer, spinal anchor, intravertebral fusion device, bone clamp, or other anchor.

In one embodiment, one or more of bone anchors 300, 301, and/or 320 is formed such that stem 303 and/or 321 functions as a sheath, defining an internal chamber 308 and 323 respectively for containing a curable material. As illustrated in FIG. 3, internal chamber 308 extends along stem 303 from proximal head 305 to distal tip 302. As illustrated in FIG. 4, internal chamber 323 extends along stem 321 from proximal head 322 to distal tip 324. In a first configuration, when the curable material has not been exposed to an energy source, and for a period of time after exposure, stems 303 and 321 remain flexible to facilitate engagement of the stems within a prepared passageway or to allow angular adjustment along the axis of the stems to better facilitate connection with spinal rod 400 or other implant devices prior to completion of curing.

Figure 5:
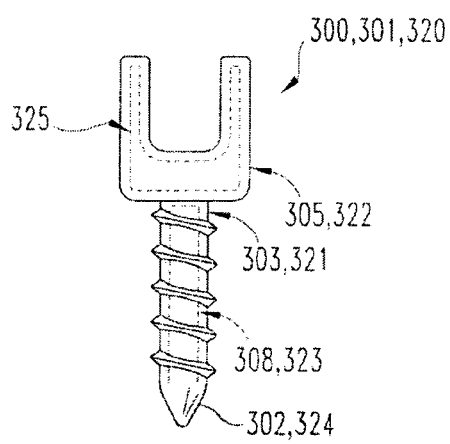
FIG. 5 is a side plan view of a bone anchor device of the spinal implant system of FIG. 2 with some features shown in phantom.

In alternative embodiments depicted in FIG. 5, heads 305 or 322 may include an internal chamber 325 with curable material to better facilitate connection of spinal rod 400 or other devices thereto either singly, or in combination with stems 303 and 321 including internal chambers 308 and 323 respectively. For example, arms 307 could be bent around the rod when flexible and then hardened to rigidly engage the rod in the passage between arms 307. Furthermore, it is contemplated that only a section of stem 303 and/or 321 may include an internal chamber with curable material to control flexibility of the respective anchor device 300, 301, and/or 320.

Figure 6:
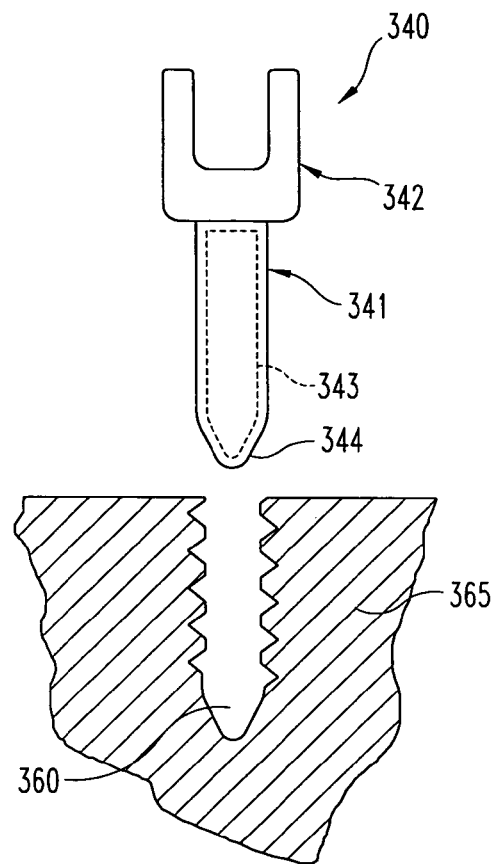
FIG. 6 is a side plan view of another embodiment bone anchor device of the spinal implant system of FIG. 2 shown in the context of a pre-formed cavity in a bony portion, which is shown in cross section.
Figure 7:
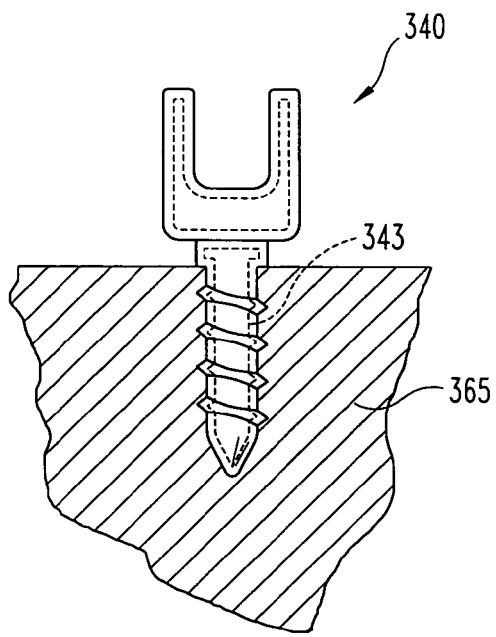
FIG. 7 is a side plan view of the embodiment of FIG. 6 with the stem of the bone anchor device positioned in the pre-formed cavity.

In yet another embodiment, depicted in FIG. 6, stem portion 341 is provided in an un-formed, malleable configuration that, upon insertion into a pre-formed cavity 360 in a bony portion 365, stem portion 341 conforms to the shape of cavity 360. After application of an appropriate dose of initiating energy and insertion of stem portion 341 into cavity 360, as depicted in FIG. 7, hardening of the curable material contained within the internal cavity 343 causes anchor 340 to durably engage bony portion 365.

Figure 8:
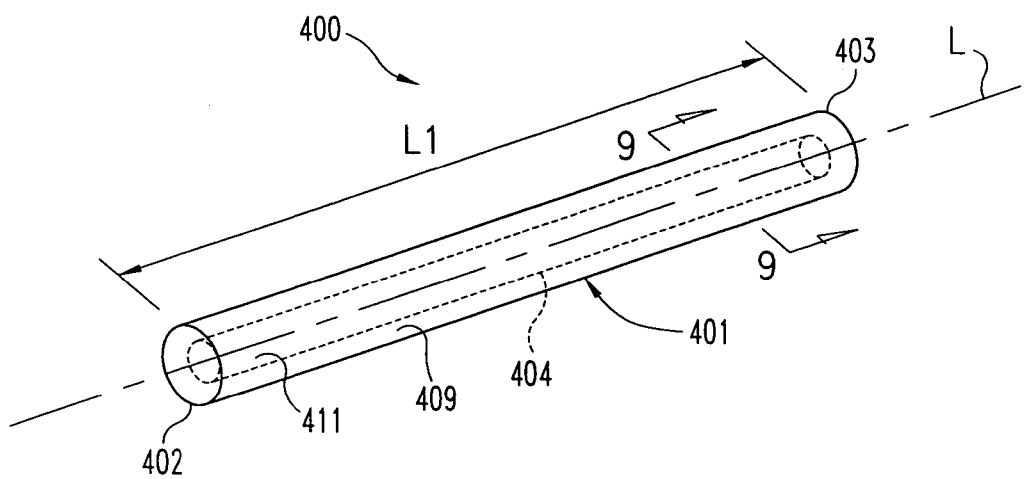
FIG. 8 is a perspective view of an elongate spinal fixation element device of the spinal implant system of FIG. 2, with some features being shown in phantom.

Spinal rod 400 of implant system 200 is illustrated in FIG. 8. Spinal rod 400 generally includes elongated body 401 extending along longitudinal axis L between first end 402 and second end 403. The length L1 of spinal rod 400 extending between first end 402 and second end 403 is typically great enough to span a distance between at least adjacent vertebral bodies, but in alternative embodiments may have a length L1 sized to span a distance between more or less than two vertebral bodies. As illustrated, spinal rod 400 contains a substantially circular or round sectional profile. It is contemplated however that the sectional profile of spinal rod 400 may vary in alternative embodiments. For example, the sectional profile of spinal rod 400 may include, but is not limited to, triangular, rectangular, hexagonal, octagonal, oval, or star shaped just to name a few possibilities.

Spinal rod 400 is sized and structured to engage with a receiving portion of a bone anchor, for example, receiving channel 306 of bone anchor devices 300, 301, 320 discussed above. When placed in receiving channel 306, spinal rod 400 may be coupled thereto create a rigid construct between two or more bone anchor devices. Spinal rod 400 may also be passively secured to a bone anchor to permit relative motion between the bone anchor and spinal rod 400.

In FIG. 8 spinal rod 400 includes internal chamber 404 extending along a substantial portion of the length L1 of rod 400. Internal chamber 404 is enclosed at least in part by sheath 409, which may comprise all or a portion of body 401, and houses curable material 411. In the embodiment illustrated, in a first configuration when curable material 411 has not been exposed to an energy source, and for a period of time after exposure, spinal rod 400 remains flexible along a substantial portion of length L1. In a second configuration, after passage of the working time following exposure to a cure-initiating energy, curable material 411 hardens and spinal rod 400 becomes more rigid or rigid along length L1.

While internal chamber 404 is shown extending along a substantial portion of length L1 of body 401, it should be understood that in alternative embodiments not shown internal chamber 404 may extend along only a portion of length L1. Furthermore, it is contemplated that body 401 may include more than one internal chamber 404 such that spinal rod 400 includes more than one flexible portion while in an initial configuration. In the embodiments where spinal rod 400 includes more than one flexible portion or where internal chamber 404 only extends along a portion of length L1, the remaining section or sections may comprise any suitable biocompatible material including, but not limited to, stainless steel, nitinol, chrome cobalt, titanium and alloys thereof, and polymers. In addition, the structure of the remaining sections of spinal rod 400 may be solid or include cannulations or passages to receive tethers, wires, or cables.

Figure 9:
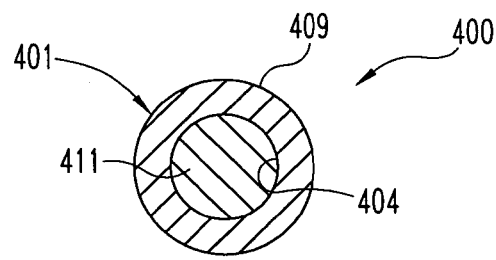
FIG. 9 is a cross sectional view of the elongate spinal fixation element device of FIG. 8 taken along view line 9-9 in FIG. 8.

Referring now to FIG. 9 there is shown a cross sectional view of spinal rod 400 viewed along view line 9-9 of FIG. 8. As illustrated, the sectional profile of spinal rod 400 is substantially circular and sheath 409 sealingly encloses curable material 411 to prevent leakage of curable material 411. Curable material 411 is structured to have an initial fluid configuration before exposure to an initiating energy and to transform to a rigid form subsequent to exposure to an energy source and a cure period. As used herein, the term "fluid" is intended to refer to a form that imparts a malleable or flexible characteristic to spinal rod 400. The application contemplates that certain solid forms, such as, for example, particulate solids or otherwise deformable solids can impart such characteristics to the device, and are therefore included within the meaning of the term "fluid." The amount of time required for transition from the flexible configuration to the rigid configuration will be dependent upon the type of material comprising curable material 411. Once in a cured state, the material is structured to provide support for all or part of a respective implant.

Spinal implant system 200 may further include crosslink device 500, shown in side elevation view with some features in phantom in FIG. 10. Crosslink device 500 includes a first branch member 502 and a second branch member 507 connected at an interconnection device 501. Interconnection device 501 may be structured to facilitate translation and/or rotation of branch members 502 and/or 507 relative to interconnection device 501 and/or each other. Alternatively, branch members 502 and/or 507 can be formed integrally as a single unit with interconnection device 501 or with one another. Branch member 502 includes a body 503 between first end 504 and second end 505. Body 503 includes internal chamber 506 enclosed by body 503 that functions as a sheath, and a curable material can be contained within internal chamber 506. Branch member 507 includes first end 509 opposite second end 510 with body 508 extending therebetween. Body 508 includes internal chamber 511 that functions as a sheath and contains a curable material.

Each of branch members 502 and 507 includes an engagement portion 512 and 513, respectively, adjacent ends 504, 509. Engagement portions 512 and 513 can be sized and structured to engage with other components of spinal implant system 200. For example, system 200 may include more than one spinal rod 400 connected to an additional set of bone screws 300 and 301, wherein each of spinal rods 400 extend parallel to each other along the spinal column of a patient. In this embodiment, engagement portions 512 and 513 engage with each of the spinal rods 400 such that crosslink device 500 extends transversely therebetween. In alternative embodiments, engagement portions 512 and 513 may be structured to engage with a bone hook, bone screw, or other anchoring device to which the spinal rod is coupled.

As illustrated, internal chambers 506 and 511 extend substantially along all the length of the respective branch members 502 and 507. Crosslink device 500 can remain flexible to facilitate interconnection of crosslink device 500 with various spinal components before the curable material hardens and rigidizes branch members 502 and 507 to create a rigid construct between crosslink device 500 and the respective implant components. In alternative embodiments not shown, internal chamber 506 and/or 511 may extend along only a portion of branch members 502 and/or 507 respectively. Additionally, it is contemplated that each of branch members 502 and/or 507 may include more than one internal chamber with curable material, and that the sheath may form all or a portion of the branch members 502, 507.

Figure 11:
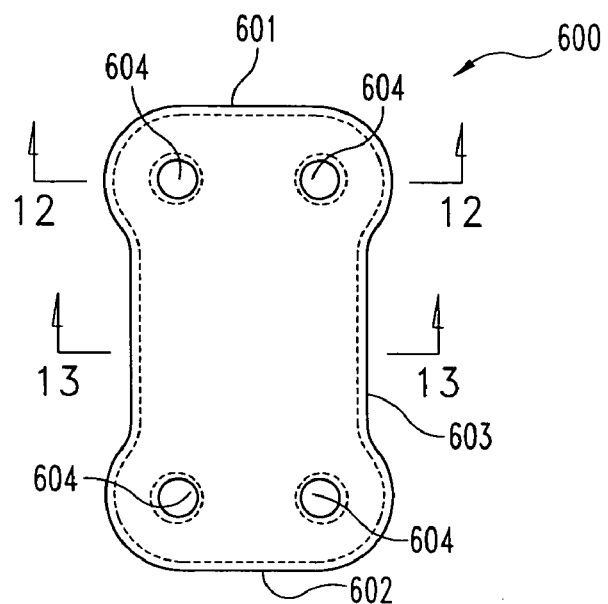
FIG. 11 is a side plan view of an embodiment of an extradiscal plate implant device.

In FIG. 11, there is shown in plan view an alternative elongate spinal fixation element 600 with some features in phantom. Fixation element 600 is in the form of a spinal plate and includes a first end portion 601 opposite a second end portion 602 and includes a body 603 extending therebetween. Fixation element 600 is generally sized and structured to extend between at least one set of adjacent vertebral bodies, but in alternative embodiments may be structured to extend across three or more vertebrae and along one or more regions of the spinal column including the cervical, thoracic, lumbar and sacral regions. Fixation element 600 includes apertures 604 extending through end portions 601 and 602. Apertures 604 are sized and structured to permit passage of an anchoring device, such as a bone screw, to engage with a respective vertebral body so that fixation element 600 may be secured thereto. Furthermore, the exterior of fixation element 600 may include one or more surface features to further promote engagement with a bony structure including intradiscal projections and fusion members, ridges and valleys, and/or a porous material.

Figure 12:
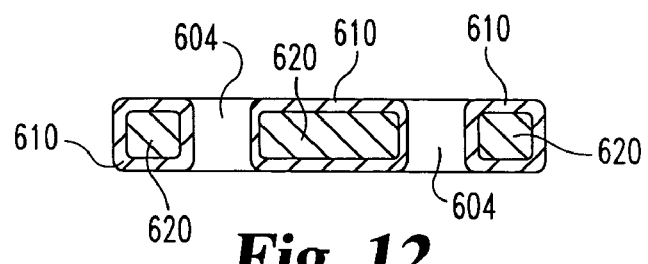
FIG. 12 is a cross sectional view of the device of FIG. 11 taken along view line 12-12 in FIG. 11.
Figure 13:
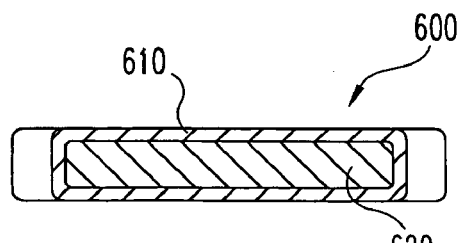
FIG. 13 is a cross sectional view of the device of FIG. 11 taken along view line 13-13 in FIG. 11.

With further reference to FIGS. 12 and 13, fixation element 600 includes sheath 610 and curable material 620 contained therein. In a first configuration, body 603 of fixation element 600 remains flexible to facilitate bending and contouring to the spinal anatomy and/or delivery to the implant site through a conduit, such as, for example, through a deployment catheter. For example, among other configurations, fixation element 600 may be bent, twisted, rolled, flattened, elongated, and/or widened in order to facilitate delivery in a minimally invasive manner or to conform to the environmental characteristics of a desired implant location. After passage of the working time following exposure of the curable material to an energy source, fixation element 600 may become rigid in the desired formation.

In alternative embodiments not shown, it is contemplated that one or more sections of plate 600 can be internally partitioned from one another such that different materials can be contained therein. For example, one or more of end portions 601 or 602 may comprise an internal chamber with curable material while body 603 extending therebetween comprises a different biocompatible material such that end portion 601 and/or 602 is flexible while in an initial configuration while body 603 is rigid or may be permanently flexible. Additionally, it is contemplated that body 603, either singly or in combination with end portion 601 and/or 602, may include an internal chamber with curable material while the other portion(s) comprise(s) a different material such that body 603 is flexible in an initial configuration while one or both of end portions 601 or 602 is rigid or permanently flexible.

Figure 14:
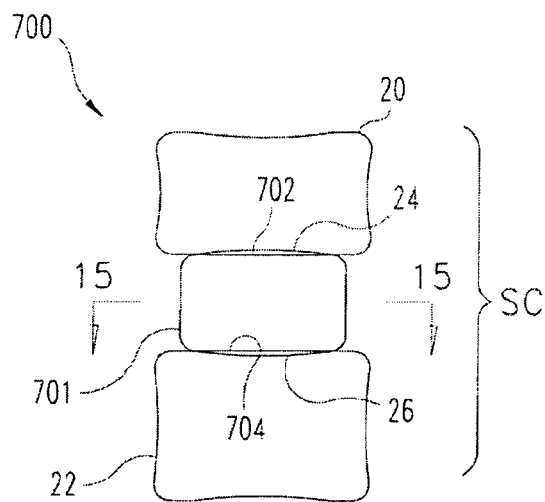
FIG. 14 is a diagrammatic side plan view of an intradiscal implant device relative to the spinal column of a patient.

With reference to FIG. 14, a device can also be used in connection with an intradiscal spinal implant. FIG. 14 shows one example of an orthopedic device and is generally directed to an intradiscal spinal implant 700 relative to the spinal column SC of a patient. Implant 700 may be used for treatment of several spinal deformities, including, but not limited to, treatment of degenerative spondylolisthesis, fracture, dislocation, scoliosis, kyphosis, spinal tumor, and/or a failed previous fusion. In the illustrated embodiment, implant 700 is disposed between a first vertebral body 20 and a second vertebral body 22, with each vertebral body including an endplate 24, 26, respectively and wherein endplates 24 and 26 are oriented toward one another. The space between endplates 24, 26 can be formed by removal or all or a portion of a disc space. Additionally, implant 700 can be employed in corpectomy procedures where one or more vertebrae are removed.

Implant 700 includes a first vertebral engaging surface 702 and a second vertebral engaging surface 704 disposed on opposite sides of body 701, wherein each surface 702, 704 is structured to engage an adjacent one of the endplates 24, 26 respectively. Surfaces 702 and 704 are depicted as relatively smooth, but may include alternative surface features in specific embodiments to facilitate engagement with endplates 24 and 26. For example, the structure of surfaces 702 and 704 may be porous and/or include ridges, valleys, spikes, knurling, and/or other securing structures as would be appreciated by one having ordinary skill in the art.

Figure 15:
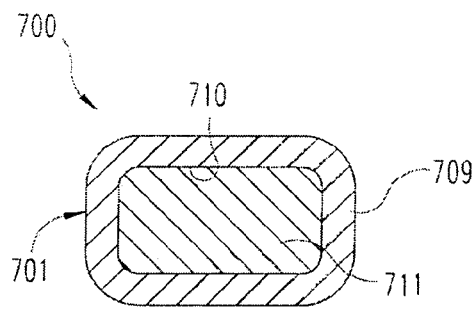
FIG. 15 is a sectional view of the implant device of FIG. 14 along view line 15-15 of FIG. 14.
Figure 16:
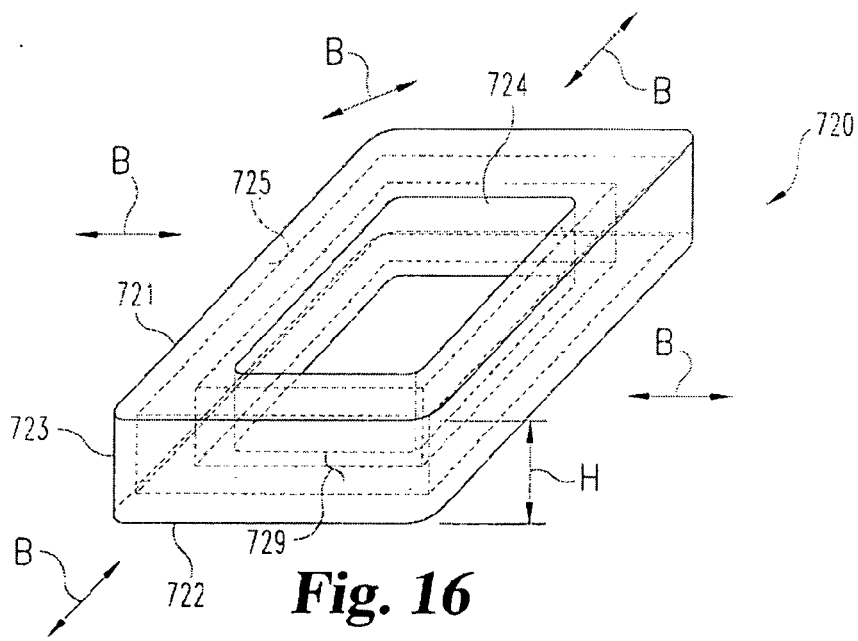
FIG. 16 is a perspective view of another embodiment intradiscal implant device with some features shown in phantom.

FIG. 15 is a sectional view of implant 700 along view line 15-15 in FIG. 14. Spinal implant 700 includes a sheath 709 about all or a portion of body 701 that forms an internal chamber 710 which contains a curable material 711. Curable material 711 is in communication with sheath 709 and is sealed in the chamber 710 so that it cannot leak or flow from out of sheath 709 and/or body 701. However, the provision of one or more ports that are resealable to selectively allow flow of curable material 711 therethrough is not precluded. Each of sheath 709 and curable material 711 is generally structured such that implant 700 has an initial flexible, bendable or formable configuration. However, after curable material 711 is exposed to an initiating energy, and following a working time, it hardens, or rigidizes, and creates a rigid implant.

The implant devices in FIGS. 16-19 are alternative examples of intradiscal implant devices that may be used for treatment of the spinal deformities as listed above in regard to spinal implant 700. Implant 720 is shown in a perspective view in FIG. 16. Implant 720 can be sized and shaped to occupy all or substantially all of a spinal disc space and can be implanted in an anterior, antero-lateral or lateral procedure. Implant 720 includes a first vertebral engaging surface 721 opposite a second vertebral engaging surface 722 and a body 723. Each of surfaces 721 and 722 are structured to engage the endplate of a vertebral body, for example, endplates 24 and 26 in FIG. 14. As such, each of surfaces 721 and 722 may include securing features such as ridges, valleys, teeth, knurling, and/or other projections or engagement structure. As is known in the art, surfaces 721 and 722 may comprise a porous material to facilitate ingress and egress of tissues to further secure implant 720 at a spinal location and/or to create fusion of adjacent vertebral bodies.

Implant 720 further comprises an opening 724 extending through body 723 from surface 721 to surface 722. In one embodiment, opening 724 may contain one or more biocompatible materials. In another embodiment, opening 724 contains a bioresorbable material such as a bone growth promoting material including, but not limited to, a bone graft material, a bone morphogenic protein (BMP), bone chips, bone marrow, a demineralized bone matrix (DBM), mesenchymal stem cells, and/or a LIM mineralization protein (LMP) or any other suitable bone growth promoting material or substance.

In the illustrated embodiment, the entire body 723 surrounding opening 724 includes sheath 729 defining internal chamber 725 containing a curable material such as curable material 711 discussed above. When the curable material has not been exposed to an energy source, and for a working time following exposure, it allows spinal implant 720 to be reconfigured to a multitude of different configurations by compression or expansion of implant 720 in a multitude of different directions, as indicated by directional arrows B. For example, among other configurations, all or part of either of surfaces 721 and 722 may be curved to seat against a wholly or partially curved spinal endplate, or the height H of the spinal implant 720 may be altered to fill a space between intervertebral bodies.

It should be understood that in alternative embodiments not shown only a section or sections of body 723 may contain internal chamber 725 with curable material in order to provide flexibility at certain locations. In these embodiments, the remainder of implant 720 not including internal chamber 725 with curable material may comprise any suitable biocompatible material as would be recognized by one having skill in the art. Additionally, in another embodiment not shown, it is contemplated that only a portion or portions of height H between surface 721 and surface 722 will include internal chamber 725 and curable material such that body 723 takes on a multi-planar configuration, with certain planes comprising curable material 711 while the remaining planes comprise any suitable biocompatible material that is the same as or that is different from the material of sheath 729. In each of the embodiments contemplated, the curable material may be exposed to an energy source to create a rigid spinal implant 720 of a desired configured formation.

Figure 17:
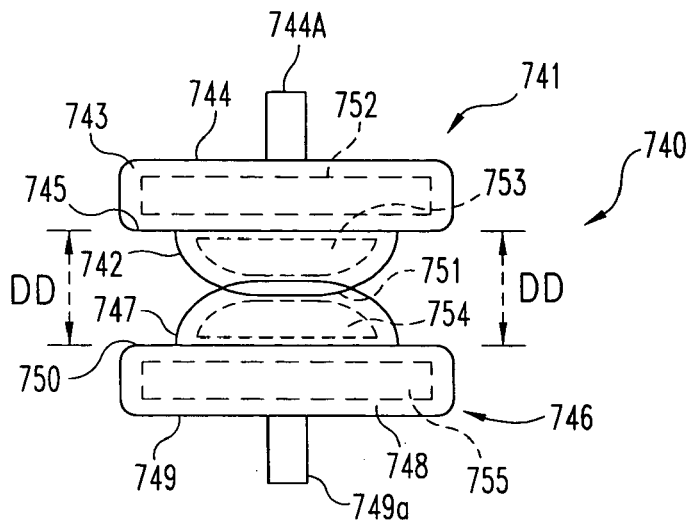
FIG. 17 is a side plan view of another embodiment intradiscal implant device with some features shown in phantom.

Referring now to FIG. 17, there is illustrated an intradiscal articulating spinal implant 740. Implant 740 includes a first articulating section 741. Section 741 includes an articulating member 742 attached to inner surface 745 of a first mounting plate 743. Implant 740 also includes a second articulating section 746 including an articulating member 747 attached to inner surface 750 of a second mounting plate 748. Each of mounting plates 743 and 748 includes a vertebral engaging surface 744 and 749, respectively. Engaging surfaces 744 and 749 may include one or more bone engagement structures 744a, 749a such as keels as shown. Other bone engagement structures are contemplated including, but not limited to, ridges, valleys, teeth, knurling, and/or other projections or engagement structure(s). It is further contemplated that engaging surfaces 744 and 749 may be porous to promote bone and/or tissue ingrowth into mounting plates 743 and 748 as would be appreciated by one having skill in the art. In another embodiment not shown, mounting plates 743 and 748 may include one or more flanges and/or apertures extending therethrough, wherein the apertures are structured to permit passage of an anchor, including but not limited to, screws, hooks, staples, and/or sutures, to secure implant 740 to each of the respective adjacent vertebral bodies. It should be understood that the addition of apertures and anchor devices may be used alone or in combination with any of the above listed bone engaging structures.

Articulating section 741 and articulating section 746 are structured to engage with one another at interface 751 such that mounting plates 743 and 748 are movable relative to one another. As one having skill in the art would recognize, when implant 740 is implanted into an intervertebral space the articulation between sections 741 and 746 creates a spinal disc-like motion, and as such, implant 740 may be used for disc replacement, among other applications. In the illustrated embodiment, articulating sections 741, 746 are arranged in a ball-and-socket type arrangement. Other embodiments contemplate other arrangements, including resiliently compressible members between mounting plates 743, 748, spring elements between plates 743, 748, or other suitable motion preserving structures.

In the embodiment illustrated, each of first mounting plate 743, articulating member 742, articulating member 747, and second mounting plate 748 is formed of material that houses respective ones of the internal chambers 752, 753, 754, and 755. Each of internal chambers 752-755 further includes a curable material such as curable material 711 such that the implant 740 has an initial flexible configuration provided by the curable material 711 and the structure of the sheath material. In another embodiment, only one of articulating sections 741 or 746 may include one or both of the internal chambers 752 and 753 or 754 and 755 and the associated curable material therein. Still, in another embodiment, one or more of the portions comprising articulating sections 741 and 746 may include its respective internal chamber and curable material 711. For example, one or more of mounting plates 743 and 748 may include internal chamber 752 or 755 and curable material such that one or more of mounting plates 743 and 748 may be configured to matingly engage with the natural or formed surface characteristics of an adjacent vertebral endplate. In another example, one or more of articulating members 742 and 747 includes curable material within the respective internal chamber 753 or 754 such that the one or more of articulating members 742 and 747 is configurable, for example, to change the distance DD between mounting plates 743 and 748 to facilitate insertion into the intradiscal space. It is further contemplated that any of the articulating members 742 and 747 and any of the mounting plates 743 and 748 may include the flexible configuration singly or in combination with any of the other implant components. In each of the embodiments contemplated, the curable material may be exposed to an energy source prior to insertion into a desired in vivo location to create a rigid spinal implant 740 of a desired conformation after a working time.

Figure 18:
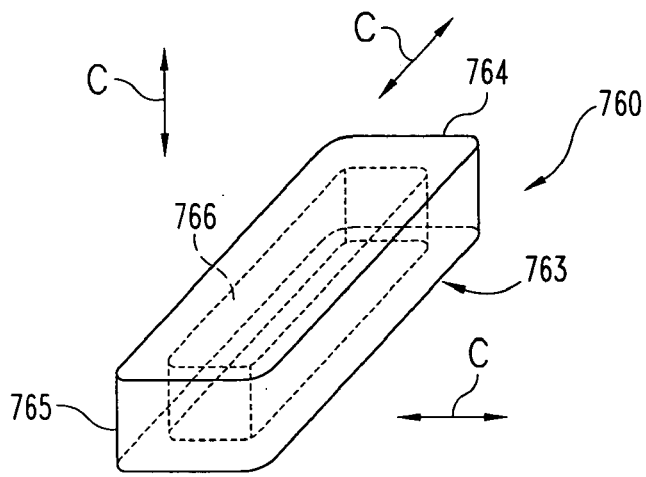
FIG. 18 is a perspective view of another embodiment intradiscal implant device with some features shown in phantom.

An implant 760 for a posterior-lateral or posterior interbody fusion procedure is illustrated in a perspective view in FIG. 18. Implant 760 may be used alone or in combination with one or more other implants in a spinal disc space. Implant 760 includes a width to accommodate insertion through a portal created posteriorly or postero-laterally, and can be elongated for orientation in the anterior-posterior directions in the disc space. Other arrangements contemplate implantation in orientations obliquely oriented to the sagittal plane or transversely to the sagittal plane in a transforaminal placement. Alternatively, implant 760 can be implanted anteriorly in side-by-side relation with another implant 760 in an anterior fusion procedure.

Spinal implant 760 includes an elongate body 763 extending between a first end 764 and a second end 765. While body 763 is shown having a substantially elongated rectangular shape and a corresponding rectangular cross section, it is contemplated that other cross section shapes are suitable, for example, including but not limited to, a substantially circular, triangular, hexagonal, or octagonal shape. The upper and lower surfaces can be convexly curved to the endplate anatomy. One or more of the sidewalls can include a concave shape or convex shape. In an embodiment not shown, spinal implant 760 may include external threading extending along all or part of body 763 between ends 764 and 765 to provided threaded engagement between adjacent vertebral bodies. Implant 760 may include other engagement structures along all or a portion of its outer surfaces, including porous structures, ridges, grooves, teeth, and/or other projections, all of which are structured to improve implant holding power and/or fusion at the implant site.

As illustrated, body 763 of spinal implant 760 forms a sheath that defines internal chamber 766, which contains a curable material therein extending along substantially all of body 763. When internal chamber 766 with curable material extends along substantially all of body 763, implant 760 can be configurable in multiple directions as indicated by directional arrows C to change its shape length, width and/or height to accommodate an implantation site or insertion portal. In another embodiment not shown, body 763 defines an internal chamber with curable material that extends along only a section of body 763. The portion of body 763 along the internal chamber is formed at least in part by a sheath, and the remainder of body 763 can be formed by any suitable biocompatible material. In certain embodiments, body 763 may include at least one cavity structured to contain a bone growth inducing agent such as, but not limited to, a bone graft material, a bone morphogenic protein (BMP), bone chips, bone marrow, a demineralized bone matrix (DBM), mesenchymal stem cells, and/or a LIM mineralization protein (LMP) or any other suitable bone growth promoting material or substance. In each of the embodiments contemplated for implant 760, the curable material in the chamber may be exposed to an energy source to create a rigid spinal implant 760 of a desired configured formation.

Figure 19:
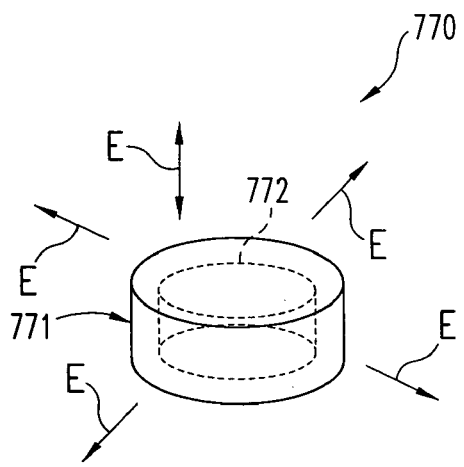
FIG. 19 is a perspective view of another embodiment intradiscal implant device with some features shown in phantom.

FIG. 19 is a perspective view of an intradiscal implant 770 that can be used for either partial or entire replacement of the nucleus pulposus to facilitate augmentation of the annulus fibrosis. Implant 770 includes a body 771 that forms a sheath which surrounds and creates internal chamber 772 to contain curable material therein. In this embodiment, implant 770 is configurable in multiple directions, as indicated by, for example, directional arrows E, which indicate height and radial adjustability of body 771 to better fit an implant site. In another embodiment not shown, implant 770 may include internal chamber 772 in only a selected portion or portions of body 771. Additionally, as illustrated, implant 770 can have a substantially cylindrical shape, but it should be understand that alternative shapes and structures for implant 770 are contemplated. For example, the size, height, and shape of implant 770 may be changed to better conform to the shape of a correspondingly prepared implant site, natural anatomic features, or insertion portal of particular size and shape. In each of the embodiments contemplated, the curable material may be exposed to an energy source prior to insertion into a desired in vivo location to create a rigid spinal implant 770 of a desired conformation after a working time.

Figure 20:
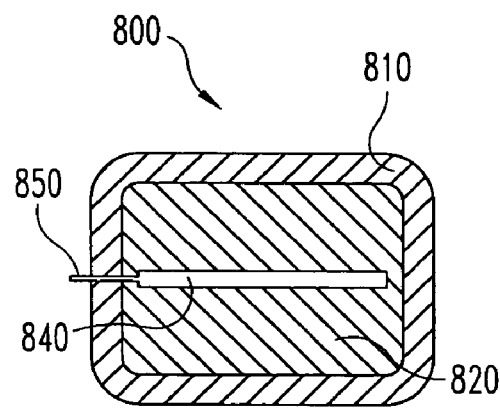
FIG. 20 is a partial cross sectional view of another embodiment of an implant device.

Another aspect of the application is depicted in FIG. 20, in which device 800 includes biocompatible sheath 810 and curable material 820 contained and sealed in sheath 810. Curable material 820 has a non-rigid form, and is transformable to a rigid form after a working time that follows application of a quantity of an initiating energy to material 820 that is effective to cure material 820. Device 800 is deformable before and during implantation within a patient, and can be configured in a wide variety of shapes and sizes for a wide variety of end uses after curing of the curable material. Device 800 also includes pressurizeable balloon 840 contained within sheath 810 such that curable material 820 is positioned outside balloon 840. When a pressurizing fluid is introduced into balloon 840 through port 850 under sufficient pressure, balloon 840 is pressurized and exerts an outward pressure on curable material 820 and sheath 810. The outward pressure can advantageously result in sheath 810 being pressed against adjacent structures, such as, for example, adjacent bony portions or adjacent implant components, to cause the device to more properly engage same and/or mate therewith. The curable material then hardens as a result of its exposure to an initiating energy prior to insertion, to create a rigid implant of a desired configured formation. As used herein, the term "balloon" is used to refer to a thin, flexible container that can be filled with a liquid or gas under pressure to expand the balloon, thereby exerting a pressure on and expanding the curable material and sheath in which it is contained.

A balloon selected for use can be constructed in a variety of ways, including using techniques that are know to be effective for making balloons for balloon angioplasty applications, and suitable materials for preparing balloons may include those that are presently used for such purposes as balloon angioplasty. Desirable materials provide an optimal combination of such properties as compliance, biostability and biocompatability, and mechanical characteristics such as elasticity and strength. Balloons can be provided in a variety of suitable forms, including those having a plurality of layers and those having a plurality of compartments when expanded. A useful balloon apparatus will include the balloon itself, together with a fluid or gas pressure applying means.

Examples of suitable materials for making balloons include, but are not limited to, polyolefin copolymers, polyethylene, polycarbonate, polyethylene terephthalate and ether-ketone polymers such as poly(etheretherketone). Such polymeric materials can be used in either unsupported form, or in supported form, e.g., by the integration of Dacron™ or other fibers. In addition, the balloon (or balloon-like structure) may comprise a wide variety of woven or nonwoven fibers, fabrics, metal mesh such as woven or braided wires, and carbon. Biocompatible fabrics or sheet material such as ePTFE and Dacron™ may also be used. In some embodiments, the balloon has metallic wires or other imageable means incorporated into it. Any material that can be seen under fluoroscopy would be acceptable. Potential materials include any metal, metal alloys, or ceramics that could be combined with a polymer. The material can be in the form of wires, a mesh, or particles incorporated into the balloon or on its surface.

Figure 21:
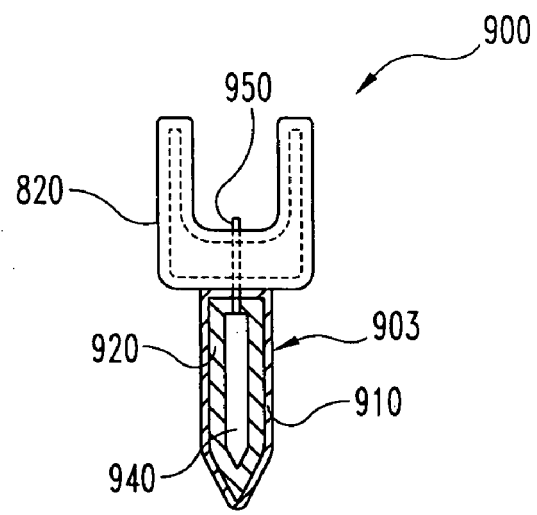
FIG. 21 is a partial cross sectional side plan view of another embodiment bone anchor device of the spinal implant system of FIG. 2, shown in the context of a pre-formed cavity in a bony portion, which is shown in cross section, wherein the stem of the bone anchor is configured to be transformed from an unexpanded form to an expanded form, said stem being depicted in this Figure in the unexpanded form.
Figure 21:
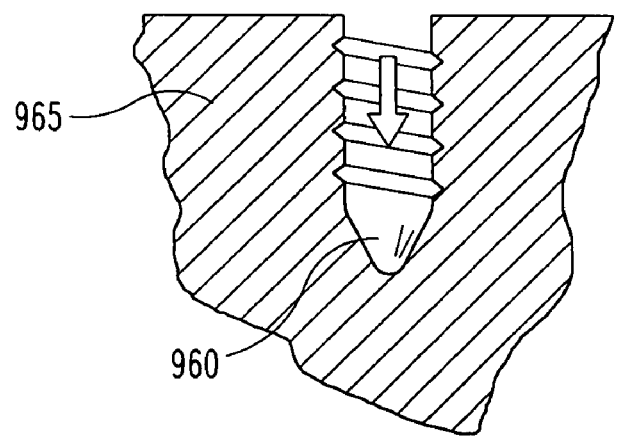
Figure 22:
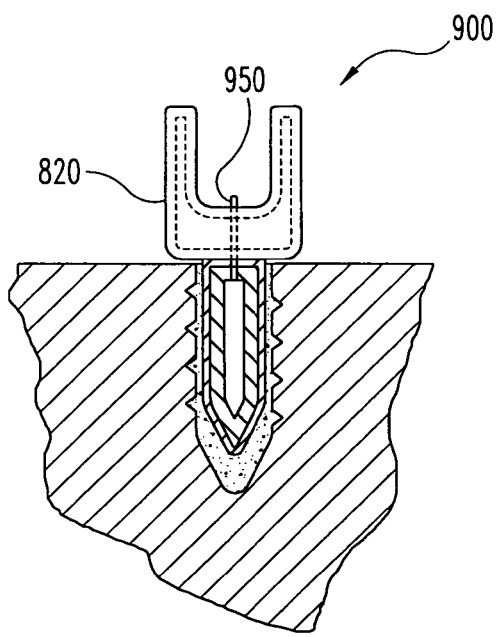
FIG. 22 is a side plan view of the bone anchor embodiment depicted in FIG. 21 with the stem of the bone anchor device positioned in the pre-formed cavity in an unexpanded, unengaged form.
Figure 23:
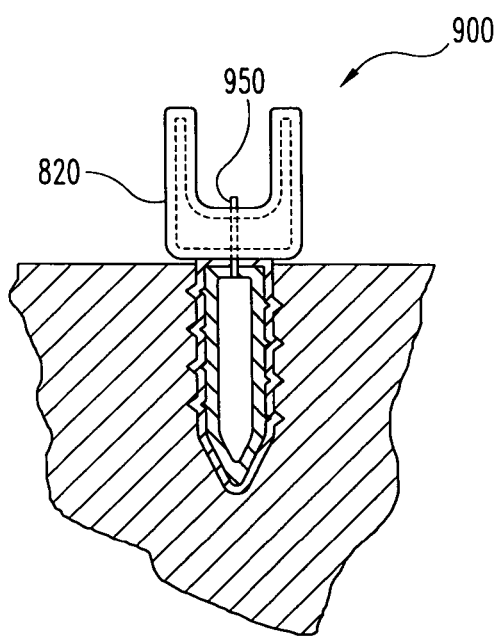
FIG. 23 is a side plan view of the bone anchor embodiment depicted in FIG. 21 with the stem of the bone anchor device positioned in the pre-formed cavity in an expanded, engaged form.

Further details regarding certain exemplary embodiments that include balloons are provided herein with reference to FIGS. 21-23. In the embodiment depicted in FIG. 21, bone anchor device 900 includes stem portion 903 that is provided in a malleable configuration and that includes sheath 910, defining an internal chamber for containing curable material 920. Internal chamber, and thus curable material 920, extends along stem 903 from proximal head 905 to distal tip 902. In a first configuration, when the curable material has not been exposed to an energy source, and for a working time following exposure, stem 903 remains flexible to facilitate engagement of stem 903 within a prepared passageway such as pre-formed cavity 960 in bony portion 965, or to allow angular adjustment along the axis of the stem to better facilitate connection with another structural component, such as, for example, spinal rod 400. Bone anchor device 900 also includes pressurizeable balloon 940 contained with sheath 910 such that curable material 920 is positioned outside balloon 940. When a pressurizing fluid, such as, for example, saline, is introduced into balloon 940 through port 950 under sufficient pressure, balloon 940 is pressurized and exerts an outward pressure on curable material 920 and sheath 910. Thus, when balloon 940 is pressurized after stem 903 is positioned within cavity 960, as shown in FIG. 22, stem 903 is caused to conform to the shape of cavity 960, as depicted in FIG. 23. When stem 903 has a desired conformation, hardening of the curable material 920 causes anchor 900 to durably engage bony portion 965.

Figure 24:
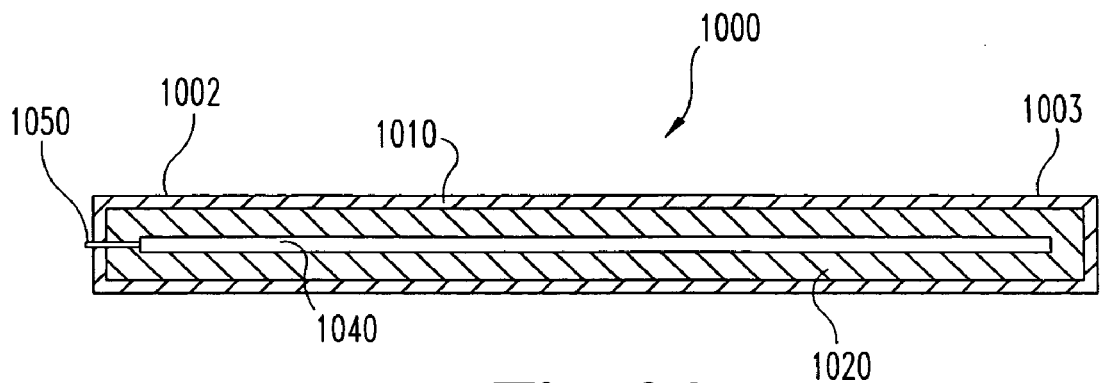
FIG. 24 is a longitudinal partial cross sectional view of another embodiment of an elongate spinal fixation element device of the spinal implant system of FIG. 2.

In the embodiment depicted in FIG. 24, spinal rod 1000 includes sheath 1010, defining an internal chamber for containing curable material 1020. Internal chamber, and thus curable material 1020, extends along rod 1000 from first end 1002 to second end 1003. In a first configuration, when the curable material has not been exposed to an initiating energy source, rod 1000 remains flexible to facilitate engagement of rod 1000 with other implant components, such as, for example, to allow angular adjustment along the axis of the rod to better facilitate connection with another structural component, such as, for example, a bone anchor or a crosslink device. Spinal rod 1000 also includes pressurizeable balloon 1040 contained with sheath 1010 such that curable material 1020 is positioned outside balloon 1040. When a pressurizing fluid, such as, for example, saline, is introduced into balloon 1040 through port 1050 under sufficient pressure, balloon 1040 is pressurized and exerts an outward pressure on curable material 1020 and sheath 1010. Thus, when balloon 1040 is pressurized, rod 1000 is caused to conform generally to the shape of adjacent structures (not shown) and/or to engage or form an interference fit with adjacent structures, such as, for example, one or more bone anchors or crosslink devices. When rod 1000 has a desired conformation, hardening of the curable material 1020 causes rod 100 to rigidize, and provide a load-bearing function. Pressurizing balloons, such as balloons 840, 940 and 1040, can be used in connection with a wide variety of other embodiments, such as, for example, in spinal devices for other intradiscal and extradiscal devices including but not limited to devices operable to movably support the vertebrae and interbody fusion devices.

Figure 25:
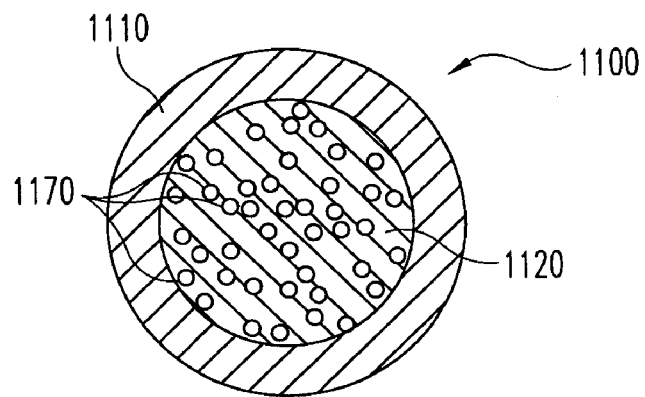
FIG. 25 is a cross sectional view of another embodiment of an elongate spinal fixation device of the spinal implant system of FIG. 2.

In FIG. 25, spinal rod 1100, depicted in cross-section, includes reinforcement member 1170 contained within sheath 1110 and embedded in curable material 1120. In the embodiment shown, reinforcement member 1170 comprises a structural matrix material composed of multiple fibers such as, for example, a matrix of carbon fibers. Alternatively, a wide variety of alternative materials and architectures can be employed for reinforcement member 1170 as would be contemplated by a person of ordinary skill in the art. For example, reinforcement member 1170 may comprise, but is not limited to, fused silica, metal or ceramic particles, PET fibers, PET mesh, and/or carbon fibers, just to name a few. Reinforcement member 1170 is structured to provide additional implant support to increase implant rigidity and strength when necessary to achieve a desired compression or other force at an implant site. While reinforcement member 1170 is shown within spinal rod 1100, it should be further appreciated that reinforcement member 1170 may be included in the other implants described and contemplated herein.

Because light and other electromagnetic radiation, and thermal energy, have limits with regard to the depth to which they can penetrate for initiating curing reactions, particularly in embodiments in which the sheath and/or the curing material is not transparent or translucent to the radiation wavelength or not good thermal conductors (in the case of a heat-initiated curable material) the application also provides devices that include internal elements for delivery of the initiating energy to the curable material.

Figure 26:
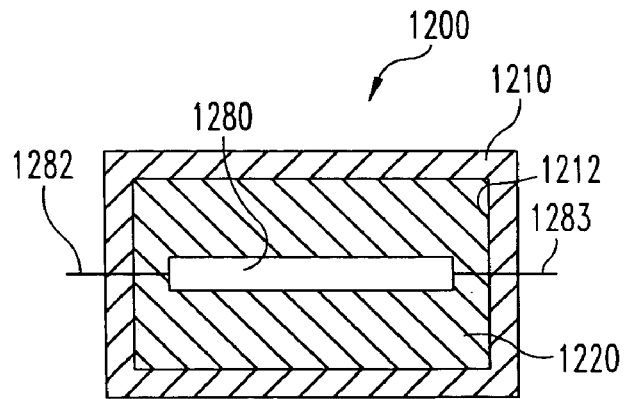
FIG. 26 is a partial cross sectional view of another embodiment of an implant device.

In the embodiment depicted in FIG. 26, device 1200 includes internal energy delivery element 1280 contained within sheath 1210 and adjacent curable material 1220. Device 1200 also includes connector 1282 for connecting energy delivery element 1280 to an external energy source (not shown). In alternate embodiments, energy delivery element 1280 can be a heating element, a fiber optic element, an antenna, an electrical element, or an element for delivering other forms of energy. Of course, the type of energy delivery element selected for use in a given embodiment will depend upon the curable material selected for use, the type of energy necessary to initiate curing of same, and the quantity of energy necessary to achieve the desired degree of curing.

In one embodiment, energy delivery element 1280 is a heat delivery element. Heat delivery elements suitable for use can comprise a variety of forms. For example, in one embodiment, the heat delivery element is a conduit formed as a loop for circulating heated media therethrough to deliver heat to the curable material, thereby initiate curing of the curable material. Of course, to deliver the thermal energy to the curable material in this embodiment, it is necessary to connect a source of heated media to one end of the loop, and to connect a drain to the other end of the loop for removing the media from the location of the implant after passage thereof through the device. Alternatively, the loop can be connection to a heated pump that forms a closed circuit with the loop, thereby reheating and re-circulating the medium for introduction back into the loop.

Another example of a heat delivery element that can be used is a resistive heating element, such as, for example, a coated tungsten wire or carbon fibers. In this embodiment, because the resistive heating element operates only upon the passage of electrical current therethrough, the heating element is oriented in a manner whereby the element forms a continuous electrical pathway. In various embodiments, the resistive heating element may be made from material with either a positive or negative temperature coefficient of resistance, e.g., electrical resistance either directly or indirectly proportionate to temperature, respectively. The temperature may be monitored by measuring the DC voltage across the resistive heating element, for the voltage is directly proportional to resistance for a given current, and the temperature coefficient of resistance is known. Alternatively, by measuring the voltage, current and phase of the drive system, the resistance of the heating element and thus its temperature can be calculated, optionally by a microprocessor or dedicated circuitry.

In order to deliver heat using a resistive heating element, it is necessary to operably connect a source of electrical current to energy delivery element 1280 via connector 1282, and pass current therethrough for a period of time sufficient to deliver a desired quantity of initiating thermal energy to curable material 1220. The source can be, for example, a battery (not shown) or an AC/DC converter. Connector 1282 and element 1280 in FIG. 26 are intended to schematically represent not only embodiments in which energy is simply introduced into energy delivery element 1280, such as, for example, by passing light into element 1280, but also embodiments that require multiple energy conduits and looped energy delivery elements, where appropriate. In this regard, in an embodiment that utilizes electrical current to provide heat or to provide electrical energy directly to the curable material, connector 1282 can comprise multiple electrical contacts for conducting a current through element 1280. For example, electrical contacts can include a concentric sliding fit connection for linking connector 1282 to a source of electrical power (not shown). These electrical contacts engage complimentary contacts on the electricity source to complete an electric circuit with a proximally located power supply for actuating the resistive heating element. Another manner of achieving multiple connections for achieving looped circuitry or other types of looped conduits, is by including optional second connector 1283. In this regard, device 1200 can include multiple connectors 1282, 1283 to provide an energy delivery circuit by connecting both connectors to separate leads from an electrical source, thereby providing an electrical circuit through device 1200.

When heat curing is used, it is preferred that the temperature of the outside of the device at the time of implant not be so high that it causes localized tissue necrosis, which occurs at approximately 45° C. This may be accomplished in several ways, such as, for example, by utilizing a heat source that sets up a temperature differential between the surface of the implant and the interior of the implant, or by utilizing a sheath 1210 composed of materials and/or having a thickness to provide thermal insulation of the adjacent tissue from heat generated by the heating element. Depending upon the make-up of the curable material 1120 selected for use, in some embodiments it is desirable to use a sheath that is composed of an electrically insulative material.

In some instances, the hardenable material is simply a material (such as a low temperature polymer) having a melting point (for crystalline materials) or a glass transition temperature (for amorphous materials) marginally above body temperature (37° C.), and is therefore solid at body temperature. In one embodiment, the melting point or glass transition temperature is between about 37° C. and about 100° C. In another embodiment, the melting point or glass transition temperature is between about 37° C. and about 75° C. In yet another embodiment, the melting point or glass transition temperature is between about 37° C. and about 50° C. In some embodiments, these low temperature materials are simply heated to the point where they are viscous and flowable and then placed at the desired location in the desired position so that the subsequent cooling of the viscous material to body temperature solidifies the device. In other embodiments, solidification of the device can be hastened by passing a cooling medium through a loop inside the device in a manner similar to that described above in connection with embodiments that utilize a heated medium. Because these materials do not need to react in vivo, they are desirable for their relative inertness.

In other alternative embodiments, the heat delivery element can comprise an RF antenna, an ultrasound transducer, a microwave antenna or a waveguide capable of converting these respective forms of energy to heat energy for delivery to the curable material. A person skilled in the art will also appreciate that, if a reinforcement member, such as reinforcement member 1170, is included in the device that is made from an electrically conductive material or a material suitable for use as an RF antenna, an ultrasound transducer, a microwave antenna or a waveguide, the reinforcement member can be utilized both to provide a reinforcement function and also to operate as a heating element.

In another embodiment, curable material 1220 is a photocurable material, and energy delivery element 1280 is a light delivery element. As used herein, the term "photocurable" is intended to refer to a material of the type for which the application of electromagnetic energy at a wavelength within the visible light spectrum initiates curing. In such an embodiment, the energy delivery element can be a fiber optic element, or can be composed of other material that effectively transmits light. In one embodiment, internal element 1280 is a transparent or translucent conduit defining an open cavity (i.e., for temporary insertion of a light source). In another embodiment, sheath 1210 has an internal surface 1212, oriented toward curable material 1220, that is effective to reflect at least a portion of the light emitted by element 1280.

In an embodiment that utilizes light energy to initiate cure, the light can be delivered to the energy delivery element in a variety of ways. For example, the light can be provided by simply shining light from a hand held light emitter onto an exposed portal capable of delivering the light into the energy delivery element, such as, for example, a fiber optic cable. Alternatively, light can be delivered to the element by physically connecting a light source to the element. In other embodiments, curable material 1220 is of the type for which the application of electromagnetic energy at a wavelength outside the visible light spectrum initiates curing. In this embodiment, energy delivery element 1280 comprises an electromagnetic radiation delivery element. In another embodiment, sheath 1210 has an internal surface 1212, oriented toward curable material 1220, that is effective to reflect at least a portion of the electromagnetic radiation. In various embodiments, the electromagnetic radiation is, by way of non-limiting example, radio frequency radiation, x-ray radiation, infrared radiation, ultraviolet radiation and microwave radiation.

Figure 27:
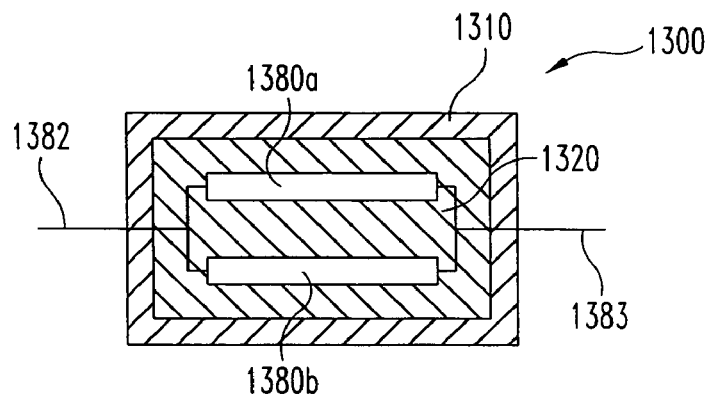
FIG. 27 is a partial cross sectional view of another embodiment of an implant device.
Figure 28:
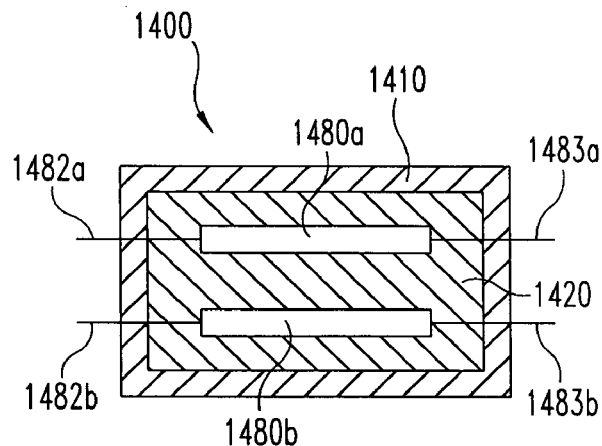
FIG. 28 is a partial cross sectional view of another embodiment of an implant device.

A device can also include multiple energy delivery elements within a single sheath, for example as shown in FIGS. 27 and 28. In FIG. 27, device 1300 includes two energy delivery elements 1380a and 1380b linked to connector 1382 for connection to an external energy source (not shown). Optional connector 1383 can also be included, and is particularly useful in embodiments in which it is desirable to include one or more of elements 1380a and 1380b in a loop or circuit, such as an electrical circuit or a heated media circulation loop, as described above. In FIG. 28, device 1400 includes two energy delivery elements 1480a and 1480b, each of which is linked to its own connector 1482a and 1482b, respectively. Optional connectors 1483a and 1483b can also be included, and are particularly useful in embodiments in which it is desirable to include one or more of elements 1480a and 1480b in a loop or circuit, such as an electrical circuit or a heated media circulation loop, as described above. Of course, other numbers of energy delivery elements contained in a single sheath can be employed, and any combination of connectors can be used that is suitable for delivering an appropriate quantity of energy to the curable material at a desired rate.

Figure 29:
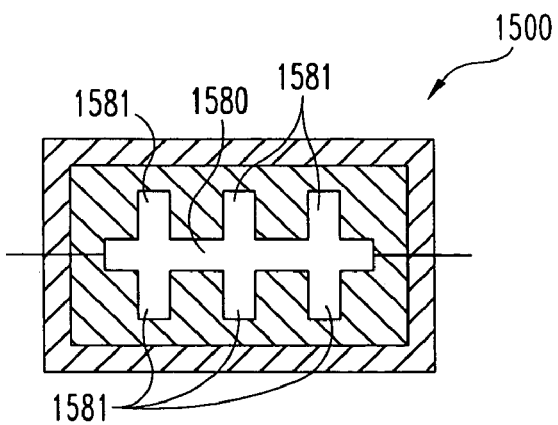
FIG. 29 is a partial cross sectional view of another embodiment of an implant device.
Figure 30:
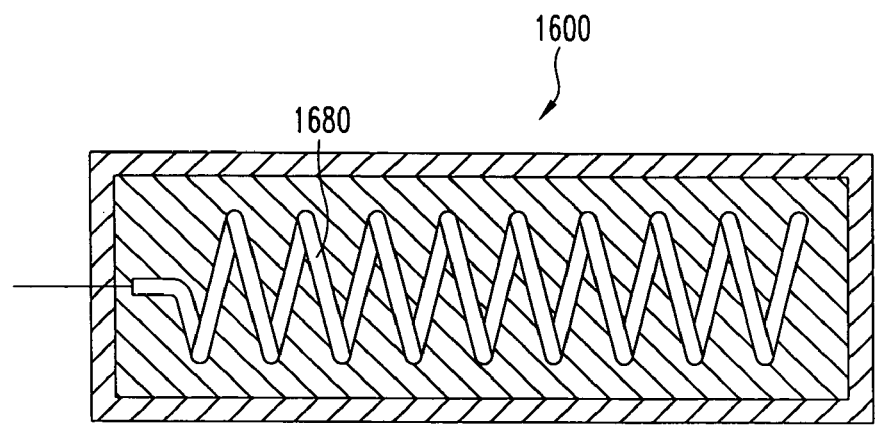
FIG. 30 is a partial cross sectional view of another embodiment of an implant device.
Figure 31:
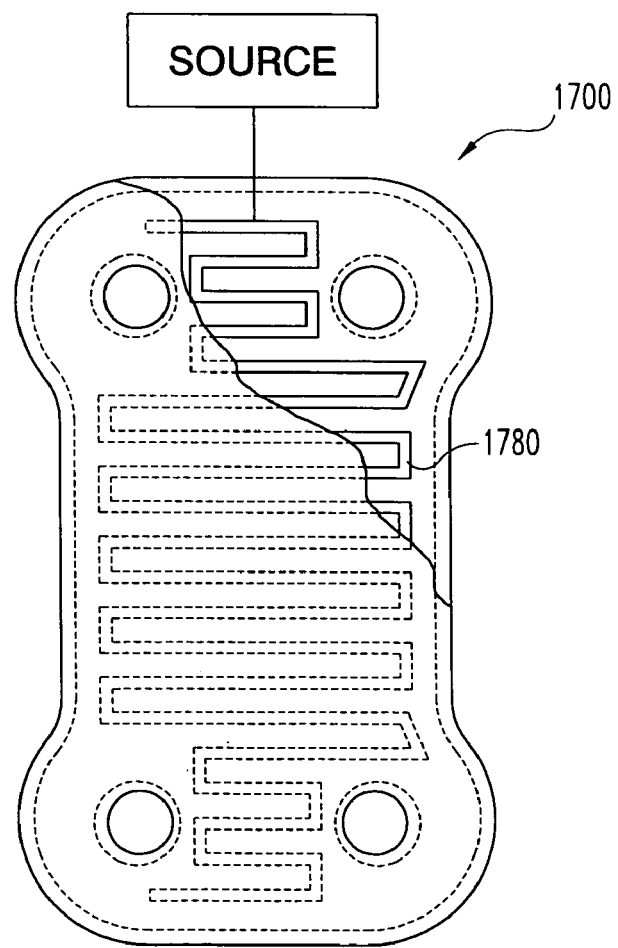
FIG. 31 is a partial cutaway side plan view of another embodiment of an implant device.

The application contemplates that the energy delivery element can take on a variety of different forms, as would occur to a person of ordinary skill in the art. For example, it is understood that a more even and thorough initiation of curing can be achieved when less distance separates an energy source or an energy delivery element and a curable material for which cure-initiation is desired. For example, in a device that is relatively thin, no internal energy delivery element is necessary as long as the sheath is formed to pass the energy therethrough, because the energy can penetrate a certain distance into the curable material. On the other hand, when a device includes a curable material having larger dimensions, it is desirable to have one or more energy delivery elements positioned such that no curable material exceeds a certain maximum distance from an energy delivery element. In one example of a manner to achieve more uniform energy delivery, a device such as device 1500 depicted in FIG. 29 includes an energy delivery element 1580 having a plurality of appendages 1581 for delivery of energy to peripheral portions of curable material 1520 from points nearer to the curable material. In another embodiment, depicted in FIG. 30, device 1600 includes a coil-shaped energy delivery element 1680. In yet another embodiment, energy delivery component 1780 depicted in FIG. 31 has a flexible zig-zag pattern. Of course, a wide variety of alternative configurations can be used in other embodiments.

The application also contemplates devices that include energy delivery elements of different types contained within the same sheath, such as, for example, one or more energy delivery elements for delivering visible light and one or more other energy delivery elements for delivering heat. In this regard, the application contemplates systems in which the curable material contained within a sheath of a given device includes a mixture of compositions for which curing is initiated by different types of energy. In other embodiments, curable materials that are initiated by different types of energy can be contained within separated compartments with a sheath or within multiple sheaths of a single device. Devices can thus be constructed that have different hardening characteristics due to different cure profiles exhibited by different curable materials. As used herein, the term "cure profile" is intended to refer to a combination of characteristics of the material that affect its curing features, such as, for example and without limitation, the type of energy that can be used to initiate curing, the quantity of energy that is required to initiate curing or to fully cure the material, the rate at which curing proceeds after it is initiated, the effect of interruption of energy exposure on curing, the effect that the quantity of energy has on the rate of curing, and the like.

Figure 32:
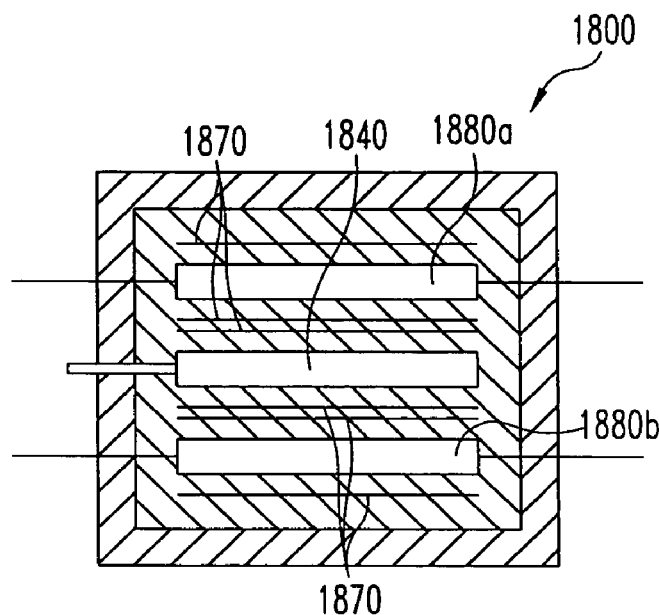
FIG. 32 is a partial cross sectional view of another embodiment of an implant device.

FIG. 32 depicts a device 1800 that includes energy delivery elements 1880a and 1880b, pressurizeable balloon 1840 and reinforcement member 1870 contained within sheath 1810. The application also contemplates devices that omit one or more of these components, as discussed herein. For example, the application contemplates a device that includes a pressurizeable balloon and reinforcement member but no energy delivery element (for example in embodiments in which energy is delivered to curable material from a point exterior to the device through the sheath). The application also contemplates a device that includes a reinforcement member and an energy delivery element but no pressurizeable balloon, and a device that includes a pressurizeable balloon and energy delivery component but no reinforcement member. Of course, the application also contemplates devices including only one of these components, as described herein.

Figure 33:
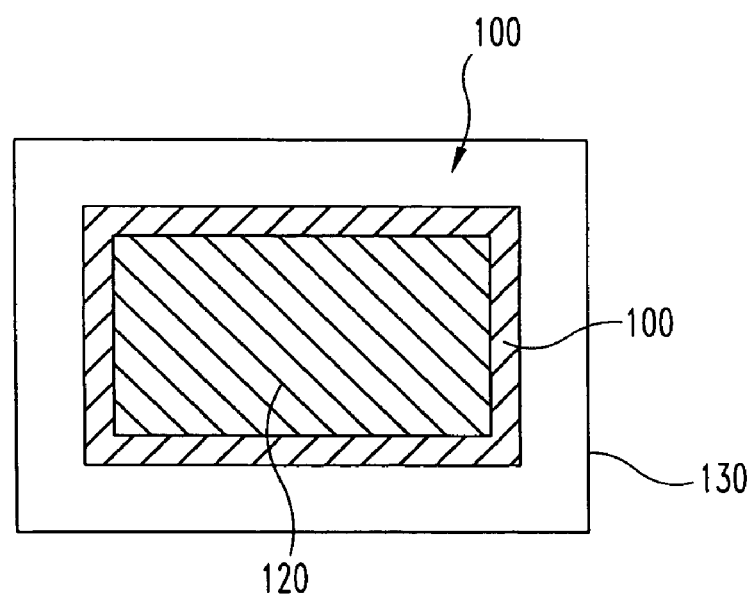
FIG. 33 is a cross sectional view of an implant device contained within a package.

A device can be made to have features whereby the device is self-contained, sealed and shelf-stable for a significant period of time. For example, in one embodiment a device includes a single-component curable composition that is pre-mixed and sealed within the sheath of the device, yet which will not begin curing until the initiating energy is applied. Such an embodiment, in addition to other excellent features, avoids complications that occur during a wet out or a 2-part mixing process during a surgery, as are required in certain curable systems proposed in the prior art. In addition, such a device can be pre-packaged and sterilized so that when medical personnel withdraw the device from the package, it is immediately ready for application of the initiating energy and implantation within a patient. Indeed, the initiating energy can be applied prior to removal of the device from the package if desired. In one embodiment, depicted in FIG. 33, device 100 is shown contained within package 130. In alternative embodiments, device 100 is sterilized prior to sealing within package 130, or device 100 and package 130 are sterilized together after placement of device 100 within package 130. The package can be configured to protect the implants from exposure to initiating energy before an anticipated implant time. The cover may be structured for removal before implantation or may be removed after placement at an in vivo location.

The application also contemplates orthopedic implants that include multiple components that are malleable and/or flexible at the time of implant, and then cured to a rigid form after being positioned at the implant site. In one embodiment, an implant includes a plurality of inventive devices that include the same curable material. In another embodiment, the respective devices include different curable materials. An implant can be constructed to have different components with different cure profiles, such that a surgeon performing the implanting procedure can achieve cure of the respective devices in a controlled fashion. For example, in certain circumstances, it might be preferred to use bone-engaging devices that harden before, or more quickly than, non-bone-engaging devices of an implant. In other embodiments, it might be preferred to use non-bone-engaging devices that harden before, or more quickly than, bone-engaging devices.

As will be appreciated by a person skilled in the art, the curable material can comprise a wide variety of compositions. In one embodiment, the curable material includes a single component epoxy. In another embodiment, the curable material comprises a photocurable material. In an exemplary embodiment when curable material is photocurable, it comprises a pre-activated epoxy adhesive with medium viscosity. One photocurable material of this nature is commercially available by the Henkel Corporation as Loctite® 3355. Among other attributes, this material has single component construction, curability upon exposure to UV light, fast cure time, and low shrinkage and resistance characteristics upon cure. This material also includes low outgassing and will cure evenly across all regions, even those that are shaded. The curable material can be provided in unitary form, e.g. in a form that need not be mixed just prior to use. Rather, after positioning the device, the curable material is exposed to initiating energy to cause polymerization through intermediation of the catalyst system. As described above, multiple different curable materials can be used, i.e., at different layers or portions of the device, so that curing with one type of initiating energy, such as, for example visible light or other type of electromagnetic radiation of one wavelength cures a portion of the device, and then exposure to another wavelength or another type of energy cures another portion. A wide variety of curable materials are contemplated by the application, and examples of curable materials that are suitable for use can be found in one or more of U.S. Pat. No. 5,837,752 to Shastri, U.S. Pat. No. 6,987,136 to Erbe et al., U.S. Pat. No. 5,681,872 to Erbe, U.S. Patent Application Publication No. 2003/0125739 to Bagga et al. and U.S. Patent Application Publication No. 2004/0230309 to Di Mauro, each of which is incorporated by reference herein in its entirety.

It is further contemplated that the devices can be provided in a product kit with fully assembled devices that need only to be exposed to initiating energy to initiate cure and implanted in to the patient following the exposure. In another form, a product kit is provided where the devices are partially assembled or unassembled. In this form, the surgeon can select the device components for assembly during the procedure to provide flexibility in selection in the type of device, the size of the device, and/or the type and amount of curable material with which to fill the device.

A method for forming and positioning a load-bearing component of an orthopedic implant device includes providing a self-contained, malleable device as described herein, applying a dose of a suitable initiating energy to the material and inserting the device to an in vivo location where the provision of load-bearing functionality is desired. If the device is provided in a sterilized form in a sealed package, the device can be removed from the package in a sterile environment, i.e., in a surgical theater, before or after exposure to cure-initiating energy, and before or after being inserted into the in vivo location.

In one manner of practicing the method, before the device is inserted to the in vivo location, it is shaped into a compacted configuration for delivery, for example, by folding or flexing the device. After the device is inserted, it can be formed to a desired shape and a desired orientation relative to a bony portion. For example, the device can be reformed, after insertion to the in vivo location, into an expanded form that is larger than the compacted form in at least one dimension. In an embodiment in which the device includes a pressurizeable balloon contained within the sheath, the reforming can include introducing a pressurizing fluid, such as, for example, saline or air, into the balloon to pressurize the balloon and exert an outward pressure on the curable material and the sheath.

In one manner of practicing the method, before the device is inserted to a desired in vivo location and configured to a desired form, the curable material is exposed to energy transmitted from a hand held or portable energy source. Energy may be in more than one form when exposure to the curable material occurs. For example, energy may be UV light and also include thermal energy, which might in some embodiments increase the rate of cure for the curable material. After a working time following application of a sufficient dose of initiating energy, the curable material rigidizes to provide a load-bearing component of an implant. After the initiating energy is applied to the material, the malleable component is inserted to a desired in vivo location and maintained in a desired orientation for a period of time sufficient for the curable material to harden, thereby forming a load-bearing component having a desired conformation for engagement with a bony portion or another component of an orthopedic implant. During the period of time that the curable material hardens, the surgeon or other medical personnel can optionally further flex or otherwise form the device to modify its position or shape. In this way, flexibility in, and control of, the shape of the device is provided.

In one embodiment, the application of energy comprises exposing the curable material to the initiating material for a time period of from about 1 second to about 30 minutes. In another embodiment, the applying comprises exposing the curable material to the initiating energy for a time period of from about 5 seconds to about 5 minutes. It is further contemplated that the working time after exposure to the energy can range, for example, from about one minute to about 60 minutes. In another form, the working time is at least about 2 minutes. In yet another form, the working time is at least about 5 minutes. In still another form, the working time is at least about 10 minutes. As used herein, the term "working time" is intended to refer to the time following application of cure-initiating energy during which the device can be worked or manipulated prior to the occurrence of a level of curing that increases the modulus to a point where working of the device is not feasible or practicable. It should be understood that the cure period for the curable material will depend upon the type of material utilized and, in certain embodiments, the cure period will be dependent upon the exposure time and intensity of energy. Additionally, the necessary exposure time and intensity of energy to achieve a desired degree of curing may depend on the properties of the curable material. For example, in an embodiment where the curable material is a photocurable material, exposure time and intensity may depend on whether the curable material is clear or opaque. It should also be appreciated that the amount of a device which needs to be exposed, whether in whole or in part, may also depend on one or both of the composition of the curable material and the type of energy used.

Figure 36:
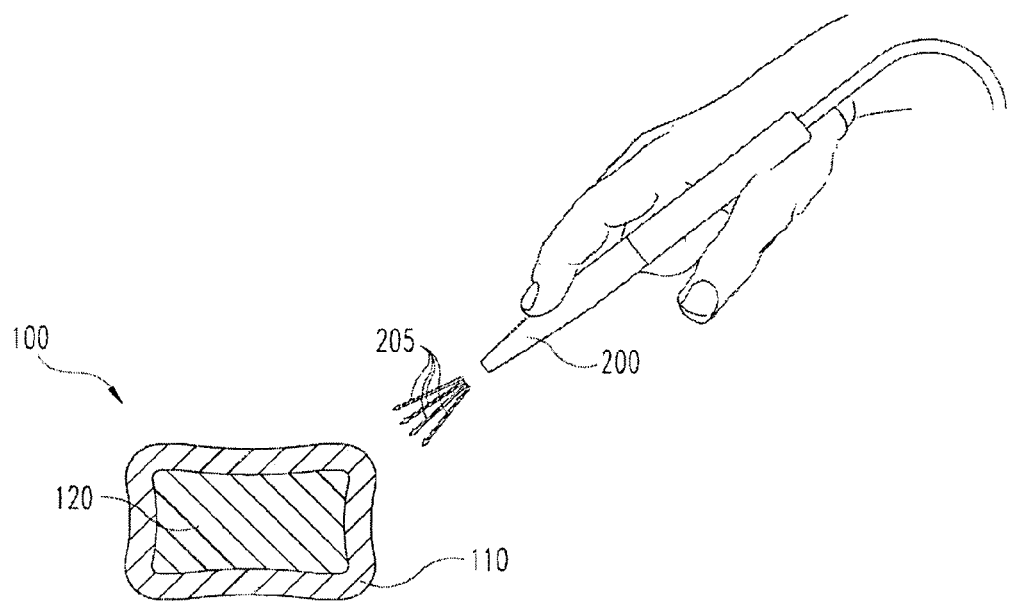
FIG. 36 is a partial cross sectional view of another embodiment of an implant device, together with a light source

When curing certain embodiments, the cure-initiating energy is provided to curable material 120 through sheath 110 from a remote source that is not physically connected to device 100. For example, energy can be transmitted to device 100 from a hand-held transmitter 200, as depicted in FIG. 36. Initiating energy, which can be, for example, light, non-visible electromagnetic radiation or heat, is represented in FIG. 36 by arrows 205. In such embodiments, it is important that sheath 110 be structured to transmit the initiating energy 205 therethrough, and also that the curable material 120 have sufficiently small dimensions that the energy 205 is able to reach all necessary portions of the curable material through the sheath to initiate curing at a desired level. For example, as discussed above, in embodiments in which the curable material is a photocurable material, the sheath can be composed of a translucent or transparent material, and the light energy used to cure the material can pass into the curable material to a sufficient degree to achieve a desired level of curing. In embodiments in which the curable material is a heat-curable material, the sheath can be composed of a heat transmitting material. When using a device containing a heat-curable material, heat conductive structures (not shown) can be positioned within the sheath to assist with delivery of heat from the sheath to the innermost portions of curable material in the device. Such structures, which operate as energy delivery elements as described above, can be, but need not be, in direct contact with the sheath.

Figure 38:
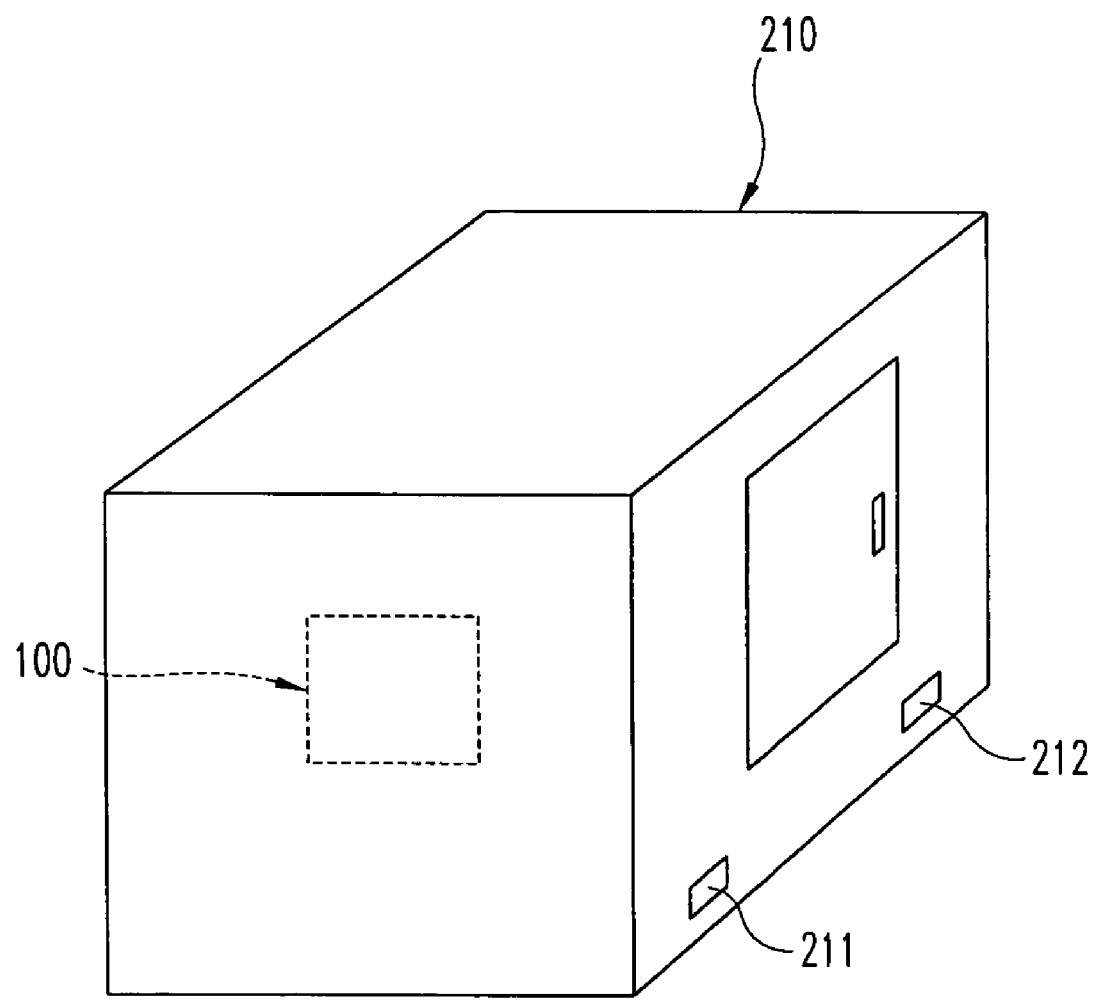
FIG. 38 is a perspective view of an implant device positioned within an energy source.

In another manner of delivering energy to curable material 120 through sheath 110, device 100 is placed inside energy source 210, as depicted in FIG. 38. For example, when employing a device that contains a heat-curable material, source 210 can be a heating device such as, for example, a convection oven. Heat can be provided by source 210 in a variety of ways known in the art, including inductive heating mechanisms or resistive electrical coils, to name a few examples. Alternatively, source 210 can provide light or other form of electromagnetic radiation to device 100 if device 100 includes a photocurable material or a material that is curable by exposure to electromagnetic radiation outside the visible light spectrum. In yet another embodiment, source 210 provides mechanical energy, such as, for example, ultrasonic energy to device 100 located therein.

In another embodiment, source 210 includes intensity controller 211 for adjusting the intensity of the energy delivered to device 100 from source 210. In another embodiment, source 210 includes timer 212. Timer 212 can operate, for example, to turn off energy source 210 at the end of a predetermined amount of time; to activate a signal, such as a light, a bell or a buzzer at the end of a predetermined amount of time; or to change the type or intensity of energy emitted by source 210.

Figure 34:
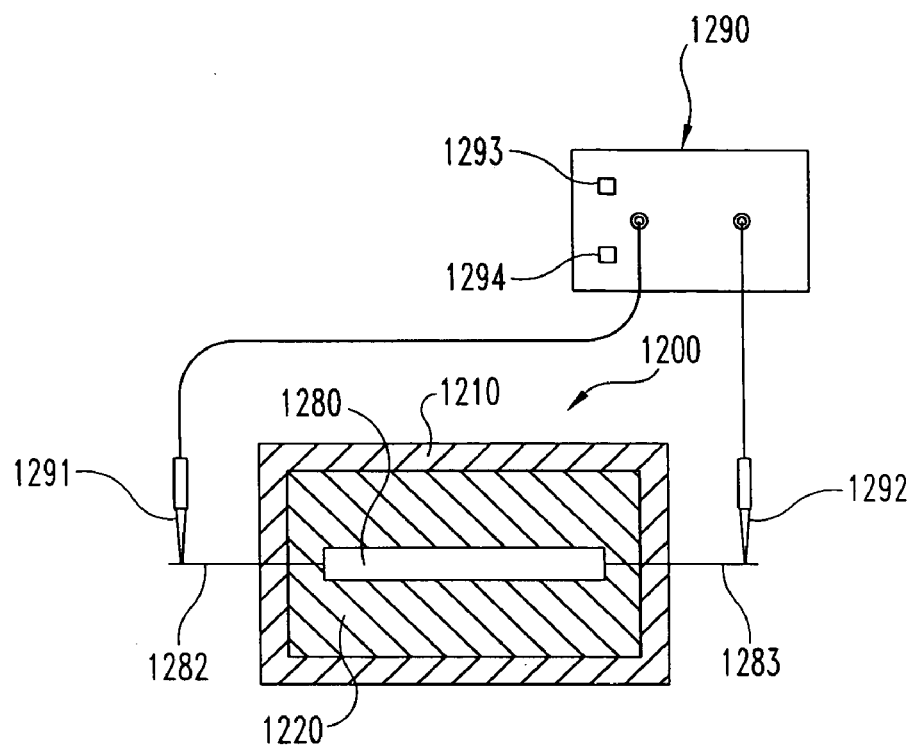
FIG. 34 is a partial cross sectional view of another embodiment of an implant device, connected to a power source.
Figure 35:
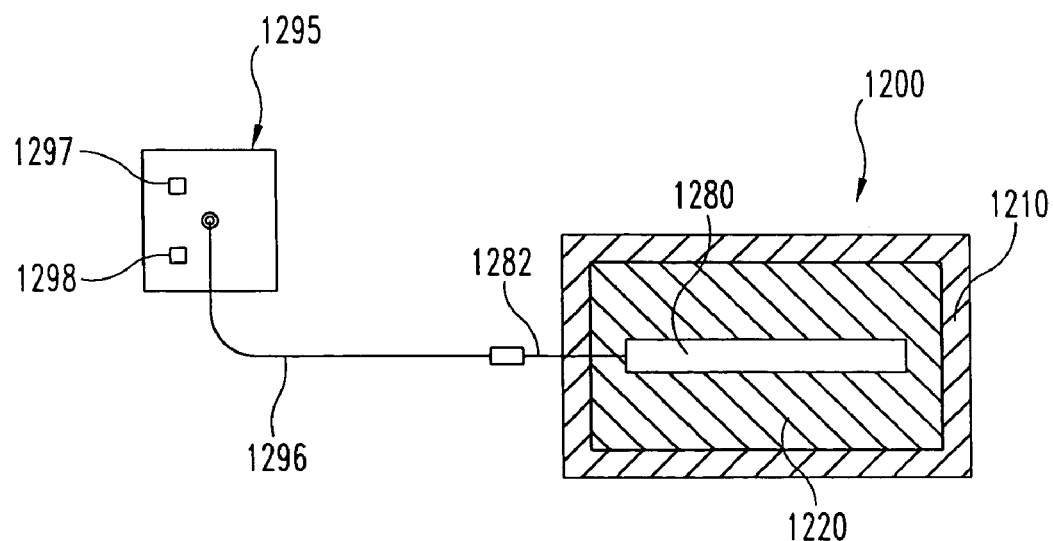
FIG. 35 is a partial cross sectional view of another embodiment of an implant device, connected to a light source.

In other embodiments, the initiating energy is introduced into the device through one or more connectors that pass through the sheath to one or more energy delivery elements contained within the sheath, as described in detail above and as depicted in FIGS. 34 and 35. With reference to FIG. 34, delivery of initiating energy to energy delivery element 1280 within an in vivo device 1200 can be achieved by connecting energy delivery leads 1291, 1292 to connectors 1282, 1283 that pass through the device's sheath 1210. For example, in the case of a resistive heating element or an electricity-delivery element, each of which require the delivery of electrical current, leads 1291, 1292 from power source 1290 can be connected to the connectors 1282, 1283 in a manner that achieves an appropriate current through the energy delivery element 1280 (or multiple elements when more than one is present in the device). With reference to FIG. 35, in the case of photo-curable embodiments, light can be provided to device 1200 by connecting energy delivery lead 1296 to connector 1282 that passes through sheath 1210 to deliver light from light source 1295 to energy delivery element 1280, which in this embodiment is a fiber optic element. Of course, additional leads (not shown) can be used to deliver light to additional elements (not shown, but as shown in connection with other embodiments) when more than one is present in the device. In other embodiments, source 1270 and source 1295 include intensity controllers 1293, 1297 for adjusting the intensity of the energy delivered to device 1200 from source 1270, 1295. In another embodiment, source 1270, 1295 includes timer 1294, 1298. Timer 1294, 1298 can operate, for example, to turn off energy source 1270, 1295 at the end of a predetermined amount of time; to activate a signal, such as a light, a bell or a buzzer at the end of a predetermined amount of time; or to change the type or intensity of energy emitted by source 1270, 1295.

The application also contemplates embodiments in which the sheath is composed of a self-sealing material, and curing is initiated by injecting into the curable material a dose of a chemical initiator effective to initiate curing.

Whether delivering light, electricity or other types of energy in the respective embodiments, leads 1291, 1292 or 1296 can be connected to a device to initiate curing, and the device can then be inserted to an in vivo location through a relatively large surgically-created opening, or through one or more relatively small openings using endoscopic equipment or radiologically-guided equipment suitable for use in minimally invasive procedures.

When a device including a pressurizeable balloon is used, a load-bearing component of an orthopedic implant device can be formed and positioned by applying a dose of the initiating energy to the material, inserting the device to an in vivo location where the provision of load-bearing functionality is desired, infusing a fluid into the balloon to pressurize the balloon, thereby pressurizing the curable material. If the device is provided in a sterilized form in a sealed package, the device can be removed from the package in a sterile environment, i.e., in a surgical theater, before or after application of the cure-initiating energy and before or after being inserted into the in vivo location.

Figure 37:
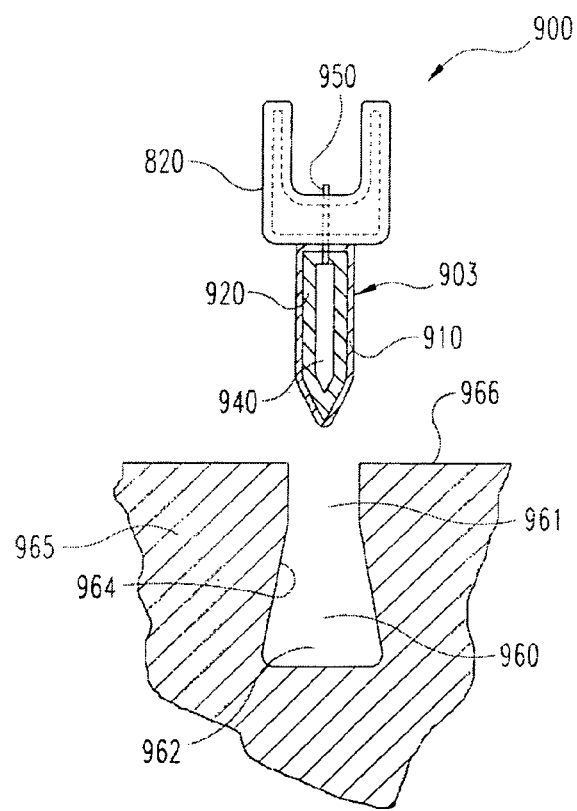
FIG. 37 is a partial cross sectional side plan view of another embodiment bone anchor device of the spinal implant system of FIG. 2, shown in the context of a pre-formed cavity in a bony portion, which is shown in cross section, wherein the stem of the bone anchor is configured to be transformed from an unexpanded form to an expanded form, said stem being depicted in this Figure in the unexpanded form.

This aspect of the application is particularly advantageous in connection with the placement of a bone anchor. As described above, an exemplary bone anchor device includes a bone engaging portion opposite a head portion. The bone engaging portion is structured to engage bony tissue, and the head portion is structured to engage an elongate implant component, such as, for example, a spinal rod. In certain embodiments, the head portion is moveable relative to the stem. The sheath can extend along all or a portion of the bone engaging portion. Because the stem is expandable, an increased degree of variability can be tolerated in the preparation of cavities in bony portions to receive the bone anchor. More specifically, it is typically necessary, before positioning a bone anchor, to provide a cavity in a bony portion to receive the stem of the anchor. The exact dimensions of the cavity, and the uniformity of the cavity features, are less critical than would be the case if the anchors were pre-formed, pre-sized and rigid. Moreover, the cavity need only have at least one anchor-retaining surface to affix an anchor therein. Indeed, as shown in FIG. 37, as long as cavity 960 has an area 961 proximal to the surface 966 of bony portion 965 that is narrower than an area 962 that is more distal to the surface 966 of bony portion 965, an anchor device as provided herein, such as, for example, anchor 900, can be used to engage bony portion 965 by pressure-fitting stem 903 of anchor 900 to walls 964 of cavity 960.

Thus, in one embodiment, a cavity is provided in a bony portion to receive the anchor device, the cavity defining at least one anchor-retaining surface configured to engage the bone anchor. After application of initiating energy to the curable material, the stem of the anchor device is passed into the cavity, and the balloon is pressurized to pressure-fit the stem to the walls of the cavity. Hardening of the curable material solidifies the engagement between the bone anchor and the bony portion. Embodiments including a pressurizeable balloon are also well suited for use as interbody devices. In this regard, pressurization of the balloon after placement of the interbody spinal device in position advantageously allows the device to better conform to the natural contours of the endplates adjacent thereto, and to spread the load-bearing function more evenly across the surfaces of the device and the endplates, which reduces the risk of pressure fractures to adjacent vertebrae.

Pressurization of the balloon can be achieved in a manner similar to pressurization of angioplasty balloons known in the art. Pressurizing fluid, such as, for example, saline or air, can be delivered to the device by a delivery conduit (not shown) connected to an in vivo-positioned device. The conduit can be connected to a port, such as, for example, ports 850, 950 or 1050 in various embodiments, by passage of the conduit through a relatively large surgically-created opening, or through a relatively small opening using endoscopic equipment or radiologically-guided equipment suitable for use in minimally invasive procedures. It is understood that the conduit and the port will include structures necessary to achieve a suitable connection for containing pressurized fluids during pressurization of the balloon.

The application also contemplates orthopedic implant devices of which multiple components are formed using curable devices described herein. For example, in certain spinal fixation devices, multiple bone anchors, spinal rods and supporting components are commonly included, a plurality of which can be formed from malleable devices as described herein. Thus, in one aspect of the application, the methods described above can further include providing a second curable device, applying a dose of initiating energy to the curable material of the second curable device and inserting the second curable device to an in vivo location where the provision of load-bearing functionality is desired. The second curable device can exhibit the same curing profile as the first component, or can optionally exhibit a different curing profile than the first component.

In another aspect of the application, there is provided an orthopedic implant kit that includes (1) a device including a biocompatible sheath and a curable material having a non-rigid form contained and sealed in the sheath, wherein the material is transformable to a rigid form after application of a quantity of an initiating energy to the material effective to fully cure the material; and (2) instructions, recorded in a tangible medium, for applying a cure-initiating energy to the curable material and then positioning the device in an in vivo location where the provision of load-bearing functionality is desired. The instructions can be customized for application to devices of a wide variety of different embodiments, and can also include alternate instructions for a given device, which provides flexibility to the surgeon using the device.

While multiple embodiments have been illustrated and described in detail in the drawings and foregoing description, the same is to be considered illustrative and not restrictive in character, it being understood that only selected embodiments have been shown and described and that all changes, equivalents, and modifications as would occur to those skilled in the art and that come within the scope of the inventions described herein or defined by the following claims are desired to be protected. Any theory, mechanism of operation, proof, or finding stated herein is meant to further enhance understanding of the present application and is not intended to limit the inventions in any way to such theory, mechanism of operation, proof, or finding. In addition, the various procedures, techniques, and operations may be altered, rearranged, substituted, deleted, duplicated, or combined as would occur to those skilled in the art. Further, any U.S. Patent, pending U.S. Patent Application Publication or other publication cited herein is incorporated herein by reference in its entirety as if each individual publication, patent, or patent application was specifically and individually indicated to be incorporated by reference and set forth in its entirety herein. In reading the claims, words such as the word "a," the word "an," the words "at least one," and the words "at least a portion" are not intended to limit the claims to only one item unless specifically stated to the contrary. Further, when the language "at least a portion" and/or "a portion" is used, the claims may include a portion and/or the entire item unless specifically stated to the contrary.

Any reference to a specific direction, for example, references to up, upper, down, lower, and the like, is to be understood for illustrative purposes only or to better identify or distinguish various components from one another. Any reference to a first or second vertebra or vertebral body is intended to distinguish between two vertebrae and is not intended to specifically identify the referenced vertebrae as adjacent vertebrae, the first and second cervical vertebrae or the first and second lumbar, thoracic, or sacral vertebrae. These references are not to be construed as limiting in any manner the medical devices and/or methods as described herein. Unless specifically identified to the contrary, all terms used herein are used to include their normal and customary terminology. Further, while various embodiments of medical devices having specific components and structures are described and illustrated herein, it is to be understood that any selected embodiment can include one or more of the specific components and/or structures described for another embodiment where possible.

What is claimed is:

1. An orthopedic implant device, comprising:
a biocompatible sheath;
a curable material having a non-rigid form contained and sealed in the sheath;
wherein the device is deformable before and during implantation within a patient;
wherein the curable material is transformable to a rigid form after application of a quantity of an initiating energy to the material effective to cure the material;
wherein the curable material exhibits a working time of at least 1 minute after application of the initiating energy and prior to fully transforming to the rigid form; and
a pressurizeable balloon positioned within the sheath and having a fluid-infusing port passing through the sheath, the pressurizing balloon operable, before the curable material is hardened, to receive a fluid to pressurize the balloon, thereby increasing the size of the device in at least one dimension, wherein, upon curing, the device becomes a bone anchor and wherein the bone anchor includes a bone engaging portion opposite a head portion, the bone engaging portion being structured to engage bony tissue and the head portion being structured to engage an elongate implant element, wherein the sheath extends along the bone engaging portion.

2. The device in accordance with claim 1, wherein the bone engaging portion comprises an elongate stem and wherein the head portion is moveable relative to the stem.

3. The device in accordance with claim 1 wherein the device is sterilized.

4. The device in accordance with claim 1, further comprising a package; and wherein the device is contained within the package.

5. The device in accordance with claim 4, wherein the device and the package are sterilized.

6. The device in accordance with claim 1, wherein after application of the initiating energy, the device has a working time prior to fully transforming to the rigid form of about 1 minute to about 60 minutes.

7. The device in accordance with claim 1, wherein, after application of the initiating energy, the device has a working time prior to fully transforming to the rigid form of at least about 2 minutes.

8. The device in accordance with claim 1, wherein the curable material includes a single component epoxy.

9. The device in accordance with claim 1, wherein the initiating energy is selected from the group consisting of electromagnetic radiation, thermal energy, electrical energy, chemical energy and mechanical energy.

10. The device in accordance with claim 9, wherein the electromagnetic radiation is selected from the group consisting of visible light, ultraviolet light, infrared light, gamma radiation, X-ray radiation and radio frequency radiation.

11. The device in accordance with claim 1, wherein the sheath is structured to transmit the initiating energy therethrough.

12. The device in accordance with claim 1, wherein the sheath is composed of a self-sealing material, and wherein said initiating energy comprises injecting into the curable material a dose of a chemical initiator effective to initiate curing.

13. The device in accordance with claim 1, wherein the curing is achieved at a temperature of from about 20° C. to about 70° C.

14. The device in accordance with claim 1, wherein the sheath comprises a material selected from the group consisting of polyethylene, polyester, polyamide, polyurethane, silicone, polyetheretherketone, polyacrylate, polylactide and polyglycolide.

15. The device in accordance with claim 1, wherein the sheath comprises a bioresorbable material.

16. The device in accordance with claim 1, further comprising a reinforcement member contained within the sheath to provide additional strength after curing.

17. The device in accordance with claim 16, wherein the reinforcement member is a structural matrix material.

18. The device in accordance with claim 16 wherein the matrix material comprises carbon fiber.

19. The device in accordance with claim 1, further comprising a plurality of connectors passing through the sheath.

20. An orthopedic implant device, comprising:
a biocompatible sheath;
a curable material contained within the sheath, the curable material operable, upon application of a cure-initiating energy, to harden, thereby forming a load-bearing component of an orthopedic implant, and wherein the curable material exhibits a working time of at least 1 minute after application of the energy and prior to fully transforming to the rigid form; and
an energy delivery element contained within the sheath, the energy delivery element comprising a fiber optic element operable to deliver initiating energy to the curable material.

21. The device in accordance with claim 20, wherein the device is sterilized.

22. The device in accordance with claim 20, further comprising a package; and wherein the device is contained within the package.

23. The device in accordance with claim 22, wherein the device and the package are sterilized.

24. The device in accordance with claim 20, wherein after application of the initiating energy, the device has a working time prior to fully transforming to the rigid form of about 1 minute to about 60 minutes.

25. The device in accordance with claim 20, wherein, after application of the initiating energy, the device has a working time prior to fully transforming to the rigid form of at least about 2 minutes.

26. The device in accordance with claim 20, wherein the initiating energy is electromagnetic radiation.

27. The device in accordance with claim 26, wherein the electromagnetic radiation is visible light, ultraviolet light, or infrared light.

28. The device in accordance with claim 20, wherein the curing is achieved at a temperature of from about 20° C. to about 70° C.

29. The device in accordance with claim 20, wherein the sheath comprises a material selected from the group consisting of polyethylene, polyester, polyamide, polyurethane, silicone, polyetheretherketone, polyacrylate, polylactide and polyglycolide.

30. The device in accordance with claim 20, wherein the sheath comprises a bioresorbable material.

31. The device in accordance with claim 20, further comprising a reinforcement member contained within the sheath to provide additional strength after curing.

32. The device in accordance with claim 31, wherein the reinforcement member is a structural matrix material.

33. The device in accordance with claim 31, wherein the matrix material comprises carbon fiber.

34. The device in accordance with claim 20, further comprising a plurality of fiber optic elements passing through the sheath.

* * * * *